(12) United States Patent
Steger et al.

(10) Patent No.: US 11,541,039 B2
(45) Date of Patent: Jan. 3, 2023

(54) COMPOUNDS AND THEIR USE AS THERAPEUTICALLY ACTIVE SUBSTANCES IN THE TREATMENT AND/OR REDUCING SIGNS OR SYMPTOMS OF DISEASES INVOLVING THE RETINAL PIGMENT EPITHELIUM

(71) Applicant: ENDOGENA THERAPEUTICS, INC., San Francisco, CA (US)

(72) Inventors: Matthias Steger, Zurich (CH); Alex Mueller, Zurich (CH); Mauro Marigo, Zurich (CH)

(73) Assignee: ENDOGENA THERAPEUTICS, INC., San Francisco, CA (US)

( * ) Notice: Subject to any disclaimer, the term of this patent is extended or adjusted under 35 U.S.C. 154(b) by 72 days.

(21) Appl. No.: 17/065,795

(22) Filed: Oct. 8, 2020

(65) Prior Publication Data
US 2022/0110921 A1    Apr. 14, 2022

(51) Int. Cl.
    *A61K 31/423*    (2006.01)
    *A61P 27/02*    (2006.01)
    (Continued)

(52) U.S. Cl.
    CPC .......... *A61K 31/423* (2013.01); *A61K 31/422* (2013.01); *A61P 27/02* (2018.01); *C07D 413/04* (2013.01); *C07D 413/14* (2013.01)

(58) Field of Classification Search
    CPC ...... C07D 413/04; A61K 31/423; A61P 27/02
    See application file for complete search history.

(56) References Cited

U.S. PATENT DOCUMENTS 9,815,819 B2    11/2017    Altmann et al.

FOREIGN PATENT DOCUMENTS

| AU | 2019/226198 A1 | 9/2019 |
|----|----------------|--------|
| CN | 103656742 A | 3/2014 |

(Continued)

OTHER PUBLICATIONS

Jan. 4, 2022 International Search Report issued in International Patent Application No. PCT/US2021/053577.
(Continued)

*Primary Examiner* — Kamal A Saeed
(74) *Attorney, Agent, or Firm* — Oliff PLC

(57) ABSTRACT

A method of treating and/or preventing disease wherein retinal pigment epithelium, including administering compound of formula (I)

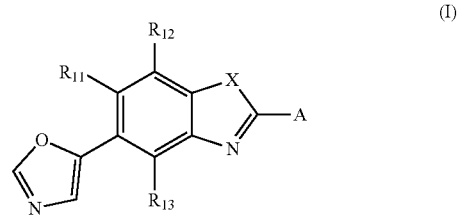

or pharmaceutically acceptable salt, racemic mixture, corresponding enantiomer or, if applicable, corresponding diastereomer, wherein: X is either NH or O, $R_{11}$, $R_{12}$ and $R_{13}$ are independently selected from consisting hydrogen group, fluoro, chloro, trifluoromethyl, methyl and difluoromethoxy, A is selected from consisting residue group of formula (II)-(VII) or (VIII)

(Continued)

-continued

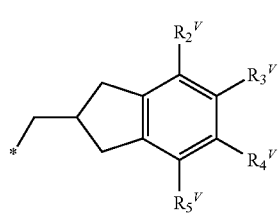
(VII)

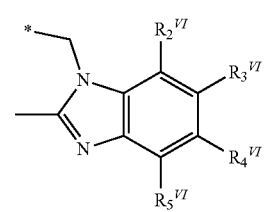

(VIII)

"*" denotes point of attachment to molecule remainder, and $R_2, R_3, R_4, R_5, R_2^I, R_3^I, R_4^I, R_5^I, R_2^{II}, R_3^{II}, R_4^{II}, R_5^{II}, R_2^{III}, R_3^{III}, R_4^{III}, R_5^{III}, R_2^{IV}, R_3^{IV}, R_4^{IV}, R_5^{IV}, R_2^V, R_3^V, R_4^V, R_5^V, R_2^{VI}, R_3^{VI}, R_4^{VI}$ and $R_5^{VI}$ are independently selected from hydrogen consisting group, linear or branched alkyl having 1-3 carbon atoms, fluoro, chloro, bromo, methoxy, ethoxy, propoxy, trifluoromethyl, 2,2,2-trifluoroethyl and difluoromethoxy and $R_6$ is selected from hydrogen consisting group, linear or branched alkyl having 1-3 carbon atoms, trifluoromethyl, and 2,2,2-trifluoroethyl.

24 Claims, 1 Drawing Sheet

(51) Int. Cl.
  *A61K 31/422*  (2006.01)
  *C07D 413/04*  (2006.01)
  *C07D 413/14*  (2006.01)

(56) References Cited

FOREIGN PATENT DOCUMENTS

| | | |
|---|---|---|
| RU | 2628697 C2 | 8/2017 |
| WO | 2015/138628 A1 | 9/2015 |
| WO | 2016/165808 A1 | 10/2016 |
| WO | 2020/140050 A1 | 7/2020 |

OTHER PUBLICATIONS

Jan. 4, 2022 Written Opinion issued in International Patent Application No. PCT/US2021/053577.

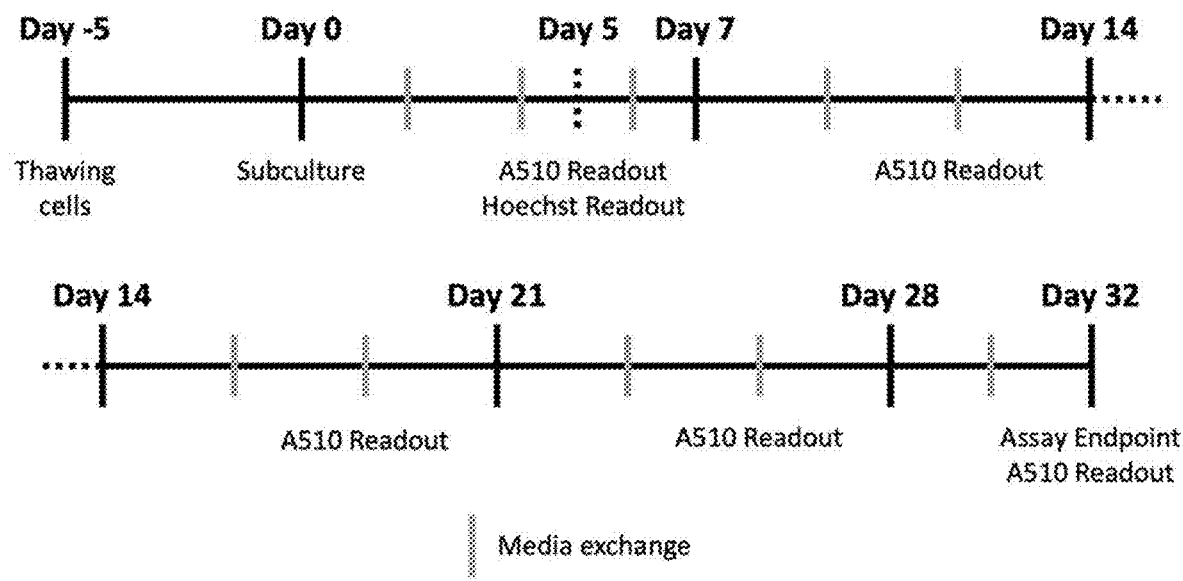

COMPOUNDS AND THEIR USE AS THERAPEUTICALLY ACTIVE SUBSTANCES IN THE TREATMENT AND/OR REDUCING SIGNS OR SYMPTOMS OF DISEASES INVOLVING THE RETINAL PIGMENT EPITHELIUM

The present invention relates to new compounds and to their use as therapeutically active substances in the treatment and/or prevention of diseases involving the retinal pigment epithelium, and in particular in the treatment and/or prevention of diseases leading to atrophy, degeneration or death of the retinal pigment epithelium that might also result in atrophy or loss of photoreceptors and/or retinal neovascularization.

An important family of diseases that involves degeneration and death of the retinal pigment epithelium (RPE) is macular degeneration. Macular degeneration is characterized by a progressive loss of central vision associated with abnormalities of Bruch's membrane, the choroid, the neural retina and/or the retinal pigment epithelium. The macula describes the central region of the retina with an approximate diameter of 0.3 to 0.5 cm. Because of its high density of cones, the macula provides detailed vision for activities such as reading, driving or recognizing faces.

So called age-related macular degeneration (AMD), the most prevalent form of macular degeneration, is associated with progressive loss of visual acuity in the central portion of the visual field, changes in color vision, and abnormal dark adaptation and sensitivity. AMD is a leading cause of irreversible vision loss in the developed world affecting approximately 2% of individuals. The prevalence of AMD increases with age and its etiology is multifactorial.

Among the key contributors to the disease and its progression are the loss of functional RPE cells and changes in their basement membrane, the Bruch's membrane. The RPE is a continuous cellular monolayer lying between the light-sensitive photoreceptors and the choroid, the blood supply of the retina. As the RPE cells perform a nourishing role to the highly metabolic photoreceptors by providing energy and growth factors, removing waste, and recycling essential compounds of the visual cycle, loss of the RPE ultimately leads to photoreceptor failure and loss.

Two principal clinical manifestations of AMD have been described as the dry or atrophic form (hereinafter referred to as dry AMD) and the wet or neovascular form (hereinafter referred to as wet AMD). Dry AMD is associated with atrophic cell death of the central retina or macula. About 10-20% of these dry AMD patients further progress to the second form, known as wet or neovascular AMD. In these advanced stages of AMD, atrophy of the RPE (geographic atrophy) and/or development of new blood vessels derived from choroidal vessels (neovascularization) further result in the death of photoreceptors and central vision loss. This loss of central vision, which is crucial for reading, the recognition of faces, and performing many daily tasks, essentially cuts the sufferer off from the world around.

No approved treatments currently exist for dry AMD or its advanced form known as geographic atrophy (GA), and many patients with neovascular AMD become legally blind despite current therapy with anti-VEGF agents such as Lucentis®. The pharmacological approaches for treating loss of vision in dry AMD caused by underlying RPE damage vary, but they are all directed to controlling the mechanisms believed to initially cause the damage (e.g. the complement system) rather than reversing the damage caused by the loss of RPE cells. Alternative approaches under investigation involve transplantation of induced pluripotent stem cells or mature RPE cells.

Drusen are tiny yellow or white accumulations of extracellular material that build up between Bruch's membrane and the retinal pigment epithelium of the eye. The presence of drusen is the hallmark of age-related macular degeneration. Recent studies of drusen have implicated a role for inflammation and other immune-mediated processes, in particular complement activation, in the aetiology of early and late forms of AMD. EP 2 302 076 discloses that Factor H protein (HF1), the major inhibitor of the alternative complement pathway, accumulates within drusen, and is synthesized locally by the retinal pigment epithelium and thus provides the administration of a medicament that decreases the amount of a variant Factor H or expression of a gene encoding Factor H in an amount effective to reduce a symptom of AMD in the patient.

U.S. Pat. No. 9,815,819 B2 relates to compounds that modulate, and preferably inhibit, activation of the alternative complement pathway as a method of treating or preventing AMD.

WO 2015/138628 relates to AAV vector constructs that are capable of, and optimized for, delivering anti-inflammatory peptides to the retina of AMD patients.

AU 2019/226198 discloses a method of producing a substantially purified culture of RPE cells suitable for transplantation.

CN 103656742 relates to a preparation method of functionalized retinal pigment epithelial cell grafts for transplantation to the retina of AMD patients.

RU 2628697 discloses a procedure to produce a cell layer from retinal pigment epithelial cells in a convenient and stable manner without using an artificial membrane and leading to high rate of engraftment when transplanted intraocularly.

PCT/US19/68768 describes the application of small molecules for triggering endogenous regeneration of photoreceptors derived from retinal stem and progenitor cells in retinal dystrophies i.e. retinitis pigmentosa. In contrast, the present invention relates to the treatment and/or prevention of RPE-related ocular diseases by stimulating pigmentation and/or growth of mammalian RPE cells.

In the case of wet AMD, there has been great progress in the development of drugs that antagonize the effects of vascular endothelial growth factor (anti-VEGF). However, these treatments do not address the damage of the RPE layer but only suppress neovascularization. Also, they are not curative but only effective at keeping the current state of the disease.

The problem of the present invention is therefore to provide therapeutic agents for the treatment and/or prevention of RPE-related diseases and particularly for the treatment of AMD.

The problem is solved by a compound of formula (I). Further preferred embodiments are subject of the dependent claims.

BRIEF DESCRIPTION OF DRAWINGS

FIG. 1: Schematic representation of RPE compound screens regimen.

It has been shown that the new compounds of formula (I) stimulate pigmentation and/or growth of mammalian RPE cells. This stimulation of pigmentation and/or growth of the endogenous RPE cells allows a controlled repair and regeneration of the retina. Thus, it is possible to prevent vision loss and/or restore vision by endogenously generating new healthy RPE cells by a compound according to the present invention. Therefore, the compound of formula (I) is useful as a therapeutically active substance in the treatment and/or prevention of diseases leading to atrophy, death or degeneration of the retinal pigment epithelium, i.e. as a medicament.

The term "RPE cells" encompasses in this context any form of proliferative and non-proliferative retinal pigment epithelial cells that can support or give rise to further differentiated functional tissues of the eye. RPE cells are smooth, pigmented and hexagonal in shape. Healthy and fully differentiated RPE cells build melanosomes, which contain the light-absorbing pigment melanin. Compounds that promote the differentiation of healthy and functional RPE cells hence lead to the presence of pigmentation.

The term "growth of mammalian RPE cells" stands for the controlled promotion of RPE cell proliferation and a corresponding increase in RPE cell numbers.

The term "prevention" refers to the prevention or reduction of signs and symptoms associated with RPE-related diseases, in particular of macular degeneration leading to vision loss in subjects who are at risk for developing the disease. In these subjects a predisposing factor may be retained, but the signs and/or symptoms of the disease do not occur or take significantly longer to develop. Further, it also includes the prevention of a further deterioration of the symptoms once the disease has occurred.

Thus, the present invention relates to a compound of formula (I)

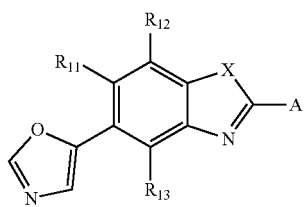

(I)

or a pharmaceutically acceptable salt, a racemic mixture, a corresponding tautomer, a corresponding enantiomer or, if applicable, a corresponding diastereomer thereof,
wherein:
X is either NH or O,
$R_{11}$, $R_{12}$ and $R_{13}$ are independently selected from the group consisting of hydrogen, fluoro, chloro, trifluoromethyl, methyl and difluoromethoxy,
A is selected from the group consisting of a residue of formula (II), (III), (IV), (V), (VI), (VII) or (VIII)

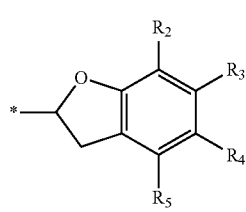

(II)

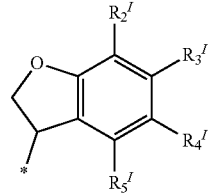

(III)

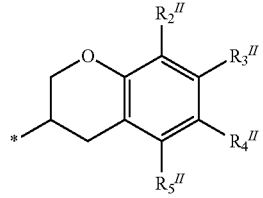

(IV)

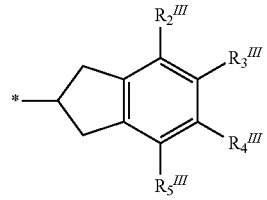

(V)

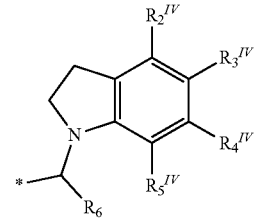

(VI)

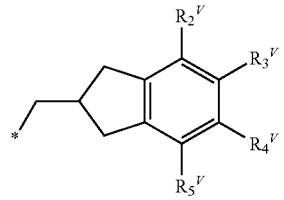

(VII)

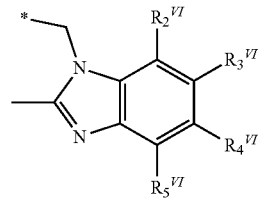

(VIII)

wherein,
"*" denotes the point of attachment to the remainder of the molecule, and
$R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3^{VI}$, $R_4^{VI}$ and $R_5^{VI}$ are independently selected from the group consisting of hydrogen, a linear or branched alkyl having 1 to 3 carbon atoms, fluoro, chloro, bromo, methoxy, ethoxy, propoxy, trifluoromethyl, 2,2,2-trifluoroethyl and difluoromethoxy and in residue of formula (VI) $R_6$ is selected from the group consisting of hydrogen, a linear or branched alkyl having 1 to 3 carbon atoms, trifluoromethyl, and 2,2,2-trifluoroethyl.

The term "pharmaceutically acceptable salt" stands for therapeutically active, non-toxic acid salt forms, which the compound according to the present invention is able to form.

In one embodiment of the present invention the asymmetric center at ring position * of the residue of formula (II), (III), (IV), (V), or the asymmetric center on the side chain of formula (VI) has the configuration as depicted below, that is a compound of formula (Ii)

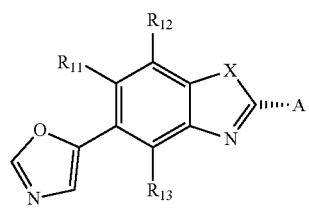

(Ii)

and A is selected from the group consisting of a residue of formula (II), (III), (IV), (V) or (VI)

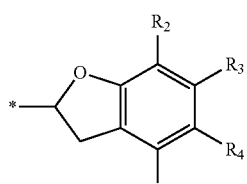

(II)

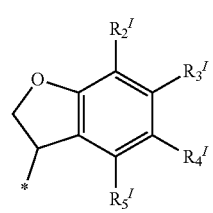

(III)

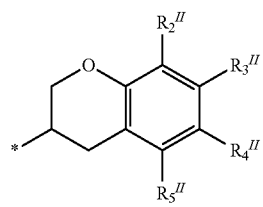

(IV)

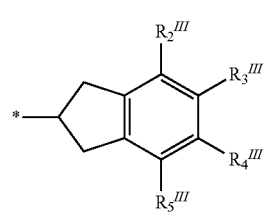

(V)

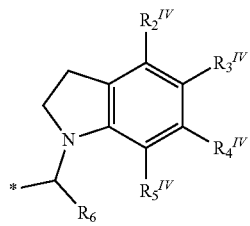

(VI)

and in case of residue of formula (VII), the chiral center ** in the compound according to the present invention has preferably the configuration as depicted below

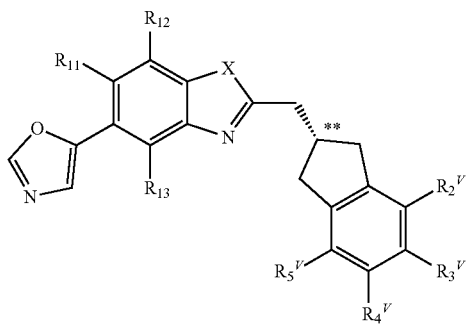

(VII)

and X, $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$, and $R_6$ have the same definition as above.

In another embodiment of the present invention the asymmetric center at ring position * of the residue of formula (II), (III), (IV), or (V), or the asymmetric center on the side chain of formula VI) is in the configuration as depicted below, that is a compound of formula (Iii)

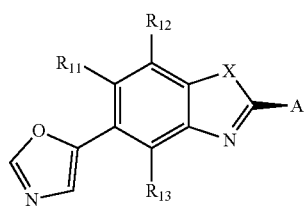

(Iii)

and A is selected from the group consisting of a residue of formula (II), (III), (IV), (V) or (VI)

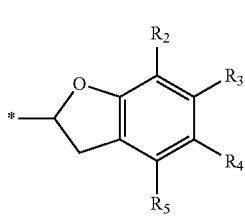

(II)

-continued

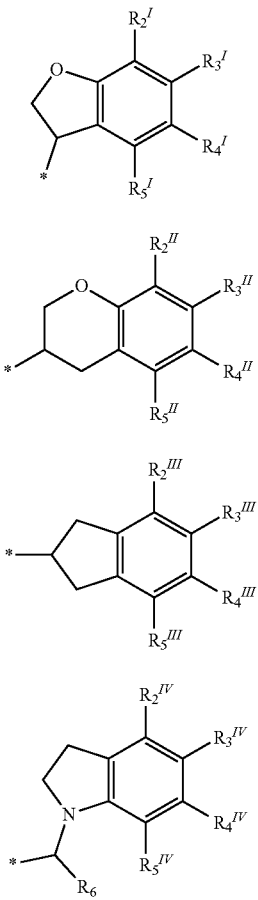

(III)

(IV)

(V)

(VI)

and in case of residue of formula (VII), the chiral center ** in the compound according to the present invention has preferably the configuration as depicted below

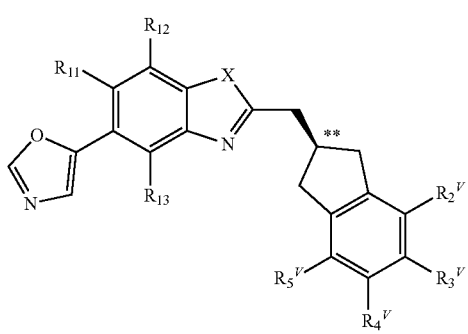

(VII)

and X, $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3^{VI}$, $R_4^{VI}$, $R_5^{VI}$ and $R_6$ have the same definition as above.

Preferably, in the compounds of formula (I) the residues $R_{11}$, $R_{12}$ and $R_{13}$ are independently selected from the group consisting of hydrogen, chloro and fluoro. Most preferably all of $R_{11}$, $R_{12}$ and $R_{13}$ are hydrogen or only one of $R_{11}$, $R_{12}$ and $R_{13}$ is selected from the group consisting of chloro and fluoro and the other residues are hydrogen. This means for example that $R_{11}$ is fluoro and $R_{12}$ and $R_{13}$ are both hydrogen.

In one embodiment of the present invention, in the compound of formula (I) X is O and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_3^{II}$, $R_2^{III}$, $R_3^{III}$, $R_4^{III}$, $R_3^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3^{VI}$, $R_4^{VI}$, $R_3^{VI}$ and $R_6$ have the same definition as above.

In another embodiment of the present invention, in the compound of formula (I) X is NH and $R_2$, $R_3$, $R_4$, $R_5$, $R_2^I$, $R_3^I$, $R_4^I$, $R_3^I$, $R_2^{II}$, $R_3^{II}$, $R_4^{II}$, $R_3^{II}$, $R_2^{III}$, $R_3^{III}$, $R_4^{III}$, $R_3^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3^{VI}$, $R_4^{VI}$, $R_5^{VI}$ and $R_6$ have the same definition as above.

The residue A is preferably unsubstituted or monosubstituted. The term unsubstituted means that all of $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3^{VI}$, $R_4^{VI}$ and $R_3^{VI}$ are hydrogen. In case the residue A is monosubstituted, one of $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3$VI, $R_4$VI and $R_5^{VI}$ is preferably selected from the group consisting of fluoro and chloro and the other residues are hydrogen. The term monosubstituted does not refer to $R_6$ in residue of formula (VI). Thus in residue of formula (VI) the term monosubstituted means that one of $R_2^{IV}$, $R_3^{IV}$, $R_4^{IV}$, $R_5^{IV}$ is different from hydrogen and $R_6$ is hydrogen, a linear or branched alkyl having 1 to 3 carbon atoms, trifluoromethyl or 2,2,2-trifluoroethyl.

In residue of formula (VI) $R_6$ is preferably hydrogen or a linear or branched alkyl having 1 to 3 carbon atoms, most preferably methyl.

One embodiment of the present invention relates to the compound of formula (Ia)

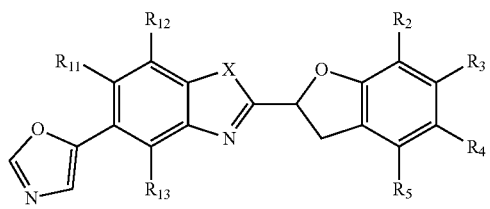

(Ia)

or a pharmaceutically acceptable salt, a racemic mixture, a corresponding enantiomer or, if applicable, a corresponding diastereomer thereof,
wherein:
X, $R_{11}$, $R_{12}$, $R_{13}$, $R_2$, $R_3$, $R_4$ and $R_5$ have the same definition as above.

Preferably, in the compounds of formula (Ia) the residues $R_{11}$, $R_{12}$ and $R_{13}$ are independently selected from the group consisting of hydrogen, chloro and fluoro. Most preferably all of $R_{11}$, $R_{12}$ and $R_{13}$ are hydrogen or only one of $R_{11}$, $R_{12}$ and $R_{13}$ is selected from the group consisting of chloro and fluoro and the other residues are hydrogen.

In one embodiment of the present invention, in the compound of formula (Ia) X is O and $R_2$, $R_3$, $R_4$, $R_5$ have the same definition as above and wherein the residue A is preferably unsubstituted or monosubstituted.

In another embodiment of the present invention, in the compound of formula (Ia) X is NH and $R_2$, $R_3$, $R_4$, $R_5$ have the same definition as above and wherein the residue A is preferably unsubstituted or monosubstituted.

Another embodiment of the present invention relates to the compound of formula (Ib)

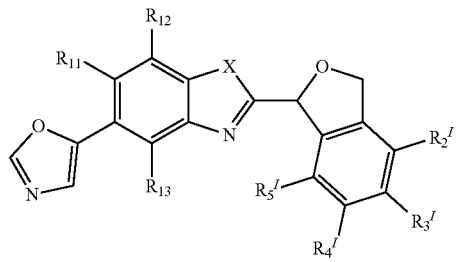

(Ib)

or a pharmaceutically acceptable salt, a racemic mixture, a corresponding enantiomer or, if applicable, a corresponding diastereomer thereof,
wherein:
X, $R_{11}$, $R_{12}$, $R_{13}$, $R_2^I$, $R_3^I$, $R_4^I$ and $R_5^I$ have the same definition as above.

Preferably, in the compounds of formula (Ib) the residues $R_{11}$, $R_{12}$ and $R_{13}$ are independently selected from the group consisting of hydrogen, chloro and fluoro. Most preferably all of $R_{11}$, $R_{12}$ and $R_{13}$ are hydrogen or only one of $R_{11}$, $R_{12}$ and $R_{13}$ is selected from the group consisting of chloro and fluoro and the other residues are hydrogen.

In one embodiment of the present invention, in the compound of formula (Ib) X is O and $R_2^I$, $R_3^I$, $R_4^I$, $R_5^I$ have the same definition as above and wherein the residue A is preferably unsubstituted or monosubstituted.

In another embodiment of the present invention, in the compound of formula (Ib) X is NH and $R_2^I$, $R_3^I$, $R_4^I$, $R_5^I$ have the same definition as above and wherein the residue A is preferably unsubstituted or monosubstituted.

Another embodiment of the present invention relates to the compound of formula (Ic)

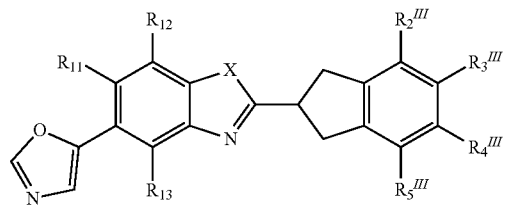

(Ic)

or a pharmaceutically acceptable salt, a racemic mixture, a corresponding enantiomer or, if applicable, a corresponding diastereomer thereof,
wherein:
X, $R_{11}$, $R_{12}$, $R_{13}$, $R_2^{II}$, $R_3^{II}$, $R_4^{II}$ and $R_5^{II}$ have the same definition as above.

Preferably, in the compounds of formula (Ic) the residues $R_{11}$, $R_{12}$ and $R_{13}$ are independently selected from the group consisting of hydrogen, chloro and fluoro. Most preferably all of $R_{11}$, $R_{12}$ and $R_{13}$ are hydrogen or only one of $R_{11}$, $R_{12}$ and $R_{13}$ is selected from the group consisting of chloro and fluoro and the other residues are hydrogen.

In one embodiment of the present invention, in the compound of formula (Ic) X is O and $R_2^{II}$, $R_3^{II}$, $R_4^{II}$, $R_5^{II}$ have the same definition as above and wherein the residue A is preferably unsubstituted or monosubstituted.

In another embodiment of the present invention, in the compound of formula (Ic) X is NH and $R_2^{II}$, $R_3^{II}$, $R_4^{II}$, $R_5^{II}$ have the same definition as above and wherein the residue A is preferably unsubstituted or monosubstituted.

Another embodiment of the present invention relates to the compound of formula (Id)

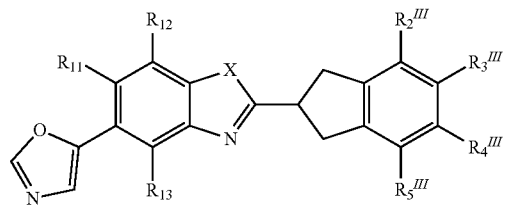

(Id)

or a pharmaceutically acceptable salt, a racemic mixture, a corresponding enantiomer or, if applicable, a corresponding diastereomer thereof,
wherein:
X, $R_{11}$, $R_{12}$, $R_{13}$, $R_2^{III}$, $R_3^{III}$, $R_4^{III}$, $R_5^{III}$ have the same definition as above.

Preferably, in the compounds of formula (Id) the residues $R_{11}$, $R_{12}$ and $R_{13}$ are independently selected from the group consisting of hydrogen, chloro and fluoro. Most preferably all of $R_{11}$, $R_{12}$ and $R_{13}$ are hydrogen or only one of $R_{11}$, $R_{12}$ and $R_{13}$ is selected from the group consisting of chloro and fluoro and the other residues are hydrogen.

In one embodiment of the present invention, in the compound of formula (Id) X is O and $R_2^{III}$, $R_3^{III}$, $R_4^{III}$, $R_5^{III}$ have the same definition as above and wherein the residue A is preferably unsubstituted or monosubstituted.

In another embodiment of the present invention, in the compound of formula (Id) X is NH and $R_2^{III}$, $R_3^{III}$, $R_4^{III}$, $R_5^{III}$ have the same definition as above and wherein the residue A is preferably unsubstituted or monosubstituted.

Another embodiment of the present invention relates to the compound of formula (Ie)

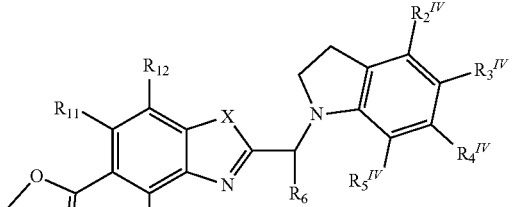

(Ie)

or a pharmaceutically acceptable salt, a racemic mixture, a corresponding enantiomer or, if applicable, a corresponding diastereomer thereof,
wherein:
X, $R_{11}$, $R_{12}$, $R_{13}$, $R_2^{IV}$, $R_3^{IV}$, $R_4^{IV}$, $R_5^{IV}$ and $R_6$ have the same definition as above.

Preferably, in the compounds of formula (Ie) the residues $R_{11}$, $R_{12}$ and $R_{13}$ are independently selected from the group consisting of hydrogen, chloro and fluoro. Most preferably all of $R_{11}$, $R_{12}$ and $R_{13}$ are hydrogen or only one of $R_{11}$, $R_{12}$ and $R_{13}$ is selected from the group consisting of chloro and fluoro and the other residues are hydrogen.

In one embodiment of the present invention, in the compound of formula (Ie) X is O and $R_2^{IV}$, $R_3^{IV}$, $R_4^{IV}$, $R_5^{IV}$ and $R_6$ have the same definition as above and wherein the residue A is preferably unsubstituted or monosubstituted.

In another embodiment of the present invention, in the compound of formula (Ie) X is NH and $R_2^{IV}$, $R_3^{IV}$, $R_4^{IV}$, $R_5^{IV}$ and $R_6$ have the same definition as above and wherein the residue A is preferably unsubstituted or monosubstituted.

Another embodiment of the present invention relates to the compound of formula (If)

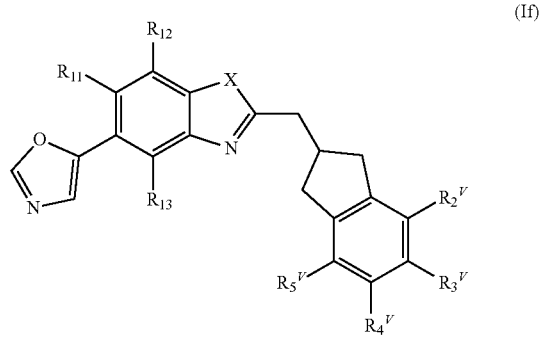

(If)

or a pharmaceutically acceptable salt, a racemic mixture, a corresponding enantiomer or, if applicable, a corresponding diastereomer thereof,
wherein:
X, $R_{11}$, $R_{12}$, $R_{13}$, $R_2^V$, $R_3^V$, $R_4^V$ and $R_5^V$ have the same definition as above.

Preferably, in the compounds of formula (If) the residues $R_{11}$, $R_{12}$ and $R_{13}$ are independently selected from the group consisting of hydrogen, chloro and fluoro. Most preferably all of $R_{11}$, $R_{12}$ and $R_{13}$ are hydrogen or only one of $R_{11}$, $R_{12}$ and $R_{13}$ is selected from the group consisting of chloro and fluoro and the other residues are hydrogen.

In one embodiment of the present invention, in the compound of formula (If) X is O and $R_2^V$, $R_3^V$, $R_4^V$, $R_3^V$ have the same definition as above and wherein the residue A is preferably unsubstituted or monosubstituted.

In another embodiment of the present invention, in the compound of formula (If) X is NH and $R_2^V$, $R_3^V$, $R_4^V$, $R_5^V$ have the same definition as above and wherein the residue A is preferably unsubstituted or monosubstituted.

Another embodiment of the present invention relates to the compound of formula (Ig)

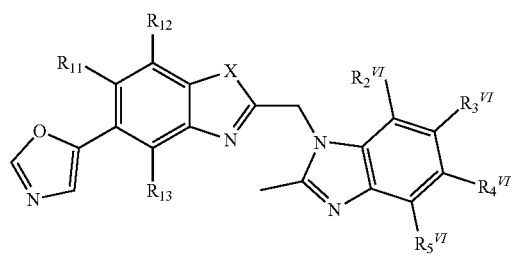

(Ig)

or a pharmaceutically acceptable salt, a racemic mixture, a corresponding enantiomer or, if applicable, a corresponding diastereomer thereof,
wherein:
X, $R_{11}$, $R_{12}$, $R_{13}$, $R_2^{VI}$, $R_3^{VI}$, $R_4^{VI}$ and $R_3^{VI}$ have the same definition as above.

Preferably, in the compounds of formula (Ig) the residues $R_{11}$, $R_{12}$ and $R_{13}$ are independently selected from the group consisting of hydrogen, chloro and fluoro. Most preferably all of $R_{11}$, $R_{12}$ and $R_{13}$ are hydrogen or only one of $R_{11}$, $R_{12}$ and $R_{13}$ is selected from the group consisting of chloro and fluoro and the other residues are hydrogen.

In one embodiment of the present invention, in the compound of formula (Ig) X is O and $R_2^{VI}$, $R_3^{VI}$, $R_4^{VI}$ and $R_5^{VI}$ have the same definition as above and wherein the residue A is preferably unsubstituted or monosubstituted.

In another embodiment of the present invention, in the compound of formula (Ig) X is NH and $R_2^{VI}$, $R_3^{VI}$, $R_4^{VI}$ and $R_5^{VI}$ have the same definition as above and wherein the residue A is preferably unsubstituted or monosubstituted.

Preferably, the compound of formula (Ia)

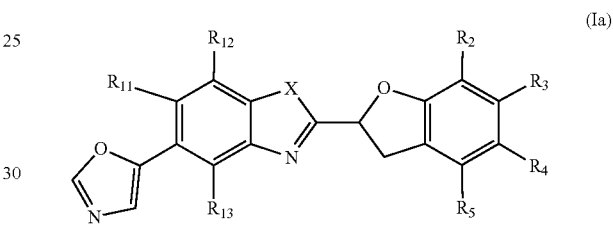

(Ia)

is selected from the group consisting of compounds of the formula (I), wherein $R_{11}$, $R_{12}$, $R_{13}$, $R_2$, $R_3$, $R_4$ and $R_5$ are as indicated in Table 1:

TABLE 1

| X | $R_{11}$ | $R_{12}$ | $R_{13}$ | $R_2$ | $R_3$ | $R_4$ | $R_5$ |
|---|---|---|---|---|---|---|---|
| N | H | H | H | H | H | H | H |
| N | H | H | H | F | H | H | H |
| N | H | H | H | H | F | H | H |
| N | H | H | H | H | Cl | H | H |
| N | H | H | H | H | $CH_3$ | H | H |
| N | H | H | H | H | $CF_3$ | H | H |
| N | H | H | H | H | $OCH_3$ | H | H |
| N | H | H | H | H | H | F | H |
| N | H | H | H | H | H | H | F |
| N | H | H | H | H | H | H | Cl |
| N | H | H | H | H | H | H | $CH_3$ |
| N | H | H | H | H | H | H | $CF_3$ |
| N | H | H | H | H | H | H | $OCH_3$ |
| N | F | H | H | H | H | H | H |
| N | F | H | H | F | H | H | H |
| N | F | H | H | H | F | H | H |
| N | F | H | H | H | Cl | H | H |
| N | F | H | H | H | $CH_3$ | H | H |
| N | F | H | H | H | $CF_3$ | H | H |
| N | F | H | H | H | $OCH_3$ | H | H |
| N | F | H | H | H | H | F | H |
| N | F | H | H | H | H | H | F |
| N | F | H | H | H | H | H | Cl |
| N | F | H | H | H | H | H | $CH_3$ |
| N | F | H | H | H | H | H | $CF_3$ |
| N | F | H | H | H | H | H | $OCH_3$ |
| N | Cl | H | H | H | H | H | H |
| N | Cl | H | H | F | H | H | H |
| N | Cl | H | H | H | F | H | H |
| N | Cl | H | H | H | Cl | H | H |
| N | Cl | H | H | H | $CH_3$ | H | H |
| N | Cl | H | H | H | $CF_3$ | H | H |

TABLE 1-continued

| X | R₁₁ | R₁₂ | R₁₃ | R₂ | R₃ | R₄ | R₅ |
|---|---|---|---|---|---|---|---|
| N | Cl | H | H | H | OCH₃ | H | H |
| N | Cl | H | H | H | H | F | H |
| N | Cl | H | H | H | H | H | F |
| N | Cl | H | H | H | H | H | Cl |
| N | Cl | H | H | H | H | H | CH₃ |
| N | Cl | H | H | H | H | H | CF₃ |
| N | Cl | H | H | H | H | H | OCH₃ |
| N | H | F | H | H | H | H | H |
| N | H | F | H | F | H | H | H |
| N | H | F | H | H | F | H | H |
| N | H | F | H | H | Cl | H | H |
| N | H | F | H | H | CH₃ | H | H |
| N | H | F | H | H | CF₃ | H | H |
| N | H | F | H | H | OCH₃ | H | H |
| N | H | F | H | H | H | F | H |
| N | H | F | H | H | H | H | F |
| N | H | F | H | H | H | H | Cl |
| N | H | F | H | H | H | H | CH₃ |
| N | H | F | H | H | H | H | CF₃ |
| N | H | F | H | H | H | H | OCH₃ |
| N | H | Cl | H | H | H | H | H |
| N | H | Cl | H | F | H | H | H |
| N | H | Cl | H | H | F | H | H |
| N | H | Cl | H | H | Cl | H | H |
| N | H | Cl | H | H | CH₃ | H | H |
| N | H | Cl | H | H | CF₃ | H | H |
| N | H | Cl | H | H | OCH₃ | H | H |
| N | H | Cl | H | H | H | F | H |
| N | H | Cl | H | H | H | H | F |
| N | H | Cl | H | H | H | H | Cl |
| N | H | Cl | H | H | H | H | CH₃ |
| N | H | Cl | H | H | H | H | CF₃ |
| N | H | Cl | H | H | H | H | OCH₃ |
| N | H | H | F | H | H | H | H |
| N | H | H | F | F | H | H | H |
| N | H | H | F | H | F | H | H |
| N | H | H | F | H | Cl | H | H |
| N | H | H | F | H | CH₃ | H | H |
| N | H | H | F | H | CF₃ | H | H |
| N | H | H | F | H | OCH₃ | H | H |
| N | H | H | F | H | H | F | H |
| N | H | H | F | H | H | H | F |
| N | H | H | F | H | H | H | Cl |
| N | H | H | F | H | H | H | CH₃ |
| N | H | H | F | H | H | H | CF₃ |
| N | H | H | F | H | H | H | OCH₃ |
| N | H | H | Cl | H | H | H | H |
| N | H | H | Cl | F | H | H | H |
| N | H | H | Cl | H | F | H | H |
| N | H | H | Cl | H | Cl | H | H |
| N | H | H | Cl | H | CH₃ | H | H |
| N | H | H | Cl | H | CF₃ | H | H |
| N | H | H | Cl | H | OCH₃ | H | H |
| N | H | H | Cl | H | H | F | H |
| N | H | H | Cl | H | H | H | F |
| N | H | H | Cl | H | H | H | Cl |
| N | H | H | Cl | H | H | H | CH₃ |
| N | H | H | Cl | H | H | H | CF₃ |
| N | H | H | Cl | H | H | H | OCH₃ |
| O | H | H | H | H | H | H | H |
| O | H | H | H | F | H | H | H |
| O | H | H | H | H | F | H | H |
| O | H | H | H | H | Cl | H | H |
| O | H | H | H | H | CH₃ | H | H |
| O | H | H | H | H | CF₃ | H | H |
| O | H | H | H | H | OCH₃ | H | H |
| O | H | H | H | H | H | F | H |
| O | H | H | H | H | H | H | F |
| O | H | H | H | H | H | H | Cl |
| O | H | H | H | H | H | H | CH₃ |
| O | H | H | H | H | H | H | CF₃ |
| O | H | H | H | H | H | H | OCH₃ |
| O | F | H | H | H | H | H | H |
| O | F | H | H | F | H | H | H |
| O | F | H | H | H | F | H | H |
| O | F | H | H | H | Cl | H | H |
| O | F | H | H | H | CH₃ | H | H |
| O | F | H | H | H | CF₃ | H | H |
| O | F | H | H | H | OCH₃ | H | H |
| O | F | H | H | H | H | F | H |
| O | F | H | H | H | H | H | F |
| O | F | H | H | H | H | H | Cl |
| O | F | H | H | H | H | H | CH₃ |
| O | F | H | H | H | H | H | CF₃ |
| O | F | H | H | H | H | H | OCH₃ |
| O | Cl | H | H | H | H | H | H |
| O | Cl | H | H | F | H | H | H |
| O | Cl | H | H | H | F | H | H |
| O | Cl | H | H | H | Cl | H | H |
| O | Cl | H | H | H | CH₃ | H | H |
| O | Cl | H | H | H | CF₃ | H | H |
| O | Cl | H | H | H | OCH₃ | H | H |
| O | Cl | H | H | H | H | F | H |
| O | Cl | H | H | H | H | H | F |
| O | Cl | H | H | H | H | H | Cl |
| O | Cl | H | H | H | H | H | CH₃ |
| O | Cl | H | H | H | H | H | CF₃ |
| O | Cl | H | H | H | H | H | OCH₃ |
| O | H | F | H | H | H | H | H |
| O | H | F | H | F | H | H | H |
| O | H | F | H | H | F | H | H |
| O | H | F | H | H | Cl | H | H |
| O | H | F | H | H | CH₃ | H | H |
| O | H | F | H | H | CF₃ | H | H |
| O | H | F | H | H | OCH₃ | H | H |
| O | H | F | H | H | H | F | H |
| O | H | F | H | H | H | H | F |
| O | H | F | H | H | H | H | Cl |
| O | H | F | H | H | H | H | CH₃ |
| O | H | F | H | H | H | H | CF₃ |
| O | H | F | H | H | H | H | OCH₃ |
| O | H | Cl | H | H | H | H | H |
| O | H | Cl | H | F | H | H | H |
| O | H | Cl | H | H | F | H | H |
| O | H | Cl | H | H | Cl | H | H |
| O | H | Cl | H | H | CH₃ | H | H |
| O | H | Cl | H | H | CF₃ | H | H |
| O | H | Cl | H | H | OCH₃ | H | H |
| O | H | Cl | H | H | H | F | H |
| O | H | Cl | H | H | H | H | F |
| O | H | Cl | H | H | H | H | Cl |
| O | H | Cl | H | H | H | H | CH₃ |
| O | H | Cl | H | H | H | H | CF₃ |
| O | H | Cl | H | H | H | H | OCH₃ |
| O | H | H | F | H | H | H | H |
| O | H | H | F | F | H | H | H |
| O | H | H | F | H | F | H | H |
| O | H | H | F | H | Cl | H | H |
| O | H | H | F | H | CH₃ | H | H |
| O | H | H | F | H | CF₃ | H | H |
| O | H | H | F | H | OCH₃ | H | H |
| O | H | H | F | H | H | F | H |
| O | H | H | F | H | H | H | F |
| O | H | H | F | H | H | H | Cl |
| O | H | H | F | H | H | H | CH₃ |
| O | H | H | F | H | H | H | CF₃ |
| O | H | H | F | H | H | H | OCH₃ |
| O | H | H | Cl | H | H | H | H |
| O | H | H | Cl | F | H | H | H |
| O | H | H | Cl | H | F | H | H |
| O | H | H | Cl | H | Cl | H | H |
| O | H | H | Cl | H | CH₃ | H | H |
| O | H | H | Cl | H | CF₃ | H | H |
| O | H | H | Cl | H | OCH₃ | H | H |
| O | H | H | Cl | H | H | F | H |
| O | H | H | Cl | H | H | H | F |
| O | H | H | Cl | H | H | H | Cl |
| O | H | H | Cl | H | H | H | CH₃ |
| O | H | H | Cl | H | H | H | CF₃ |
| O | H | H | Cl | H | H | H | OCH₃ |

Preferably, the compound of formula (Ib)

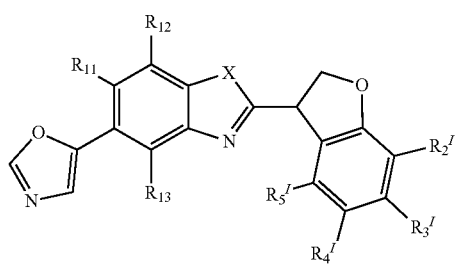

is selected from the group consisting of compounds of the formula (I), wherein $R_{11}$, $R_{12}$, $R_{13}$, $R_2^I$, $R_3^I$, $R_4^I$ and $R_5^I$ are as indicated in Table 2:

TABLE 2

| X | $R_{11}$ | $R_{12}$ | $R_{13}$ | $R_2^I$ | $R_3^I$ | $R_4^I$ | $R_5^I$ |
|---|---|---|---|---|---|---|---|
| N | H | H | H | H | H | H | H |
| N | H | H | H | F | H | H | H |
| N | H | H | H | H | F | H | H |
| N | H | H | H | H | Cl | H | H |
| N | H | H | H | H | CH$_3$ | H | H |
| N | H | H | H | H | CF$_3$ | H | H |
| N | H | H | H | H | OCH$_3$ | H | H |
| N | H | H | H | H | H | F | H |
| N | H | H | H | H | H | H | F |
| N | H | H | H | H | H | H | Cl |
| N | H | H | H | H | H | H | CH$_3$ |
| N | H | H | H | H | H | H | CF$_3$ |
| N | H | H | H | H | H | H | OCH$_3$ |
| N | F | H | H | H | H | H | H |
| N | F | H | H | F | H | H | H |
| N | F | H | H | H | F | H | H |
| N | F | H | H | H | Cl | H | H |
| N | F | H | H | H | CH$_3$ | H | H |
| N | F | H | H | H | CF$_3$ | H | H |
| N | F | H | H | H | OCH$_3$ | H | H |
| N | F | H | H | H | H | F | H |
| N | F | H | H | H | H | H | F |
| N | F | H | H | H | H | H | Cl |
| N | F | H | H | H | H | H | CH$_3$ |
| N | F | H | H | H | H | H | CF$_3$ |
| N | F | H | H | H | H | H | OCH$_3$ |
| N | Cl | H | H | H | H | H | H |
| N | Cl | H | H | F | H | H | H |
| N | Cl | H | H | H | F | H | H |
| N | Cl | H | H | H | Cl | H | H |
| N | Cl | H | H | H | CH$_3$ | H | H |
| N | Cl | H | H | H | CF$_3$ | H | H |
| N | Cl | H | H | H | OCH$_3$ | H | H |
| N | Cl | H | H | H | H | F | H |
| N | Cl | H | H | H | H | H | F |
| N | Cl | H | H | H | H | H | Cl |
| N | Cl | H | H | H | H | H | CH$_3$ |
| N | Cl | H | H | H | H | H | CF$_3$ |
| N | Cl | H | H | H | H | H | OCH$_3$ |
| N | H | F | H | H | H | H | H |
| N | H | F | H | F | H | H | H |
| N | H | F | H | H | F | H | H |
| N | H | F | H | H | Cl | H | H |
| N | H | F | H | H | CH$_3$ | H | H |
| N | H | F | H | H | CF$_3$ | H | H |
| N | H | F | H | H | OCH$_3$ | H | H |
| N | H | F | H | H | H | F | H |
| N | H | F | H | H | H | H | F |
| N | H | F | H | H | H | H | Cl |
| N | H | F | H | H | H | H | CH$_3$ |
| N | H | F | H | H | H | H | CF$_3$ |
| N | H | F | H | H | H | H | OCH$_3$ |
| N | H | Cl | H | H | H | H | H |
| N | H | Cl | H | F | H | H | H |
| N | H | Cl | H | H | F | H | H |
| N | H | Cl | H | H | Cl | H | H |
| N | H | Cl | H | H | CH$_3$ | H | H |
| N | H | Cl | H | H | CF$_3$ | H | H |
| N | H | Cl | H | H | OCH$_3$ | H | H |
| N | H | Cl | H | H | H | F | H |
| N | H | Cl | H | H | H | H | F |
| N | H | Cl | H | H | H | H | Cl |
| N | H | Cl | H | H | H | H | CH$_3$ |
| N | H | Cl | H | H | H | H | CF$_3$ |
| N | H | Cl | H | H | H | H | OCH$_3$ |
| N | H | H | F | H | H | H | H |
| N | H | H | F | F | H | H | H |
| N | H | H | F | H | F | H | H |
| N | H | H | F | H | Cl | H | H |
| N | H | H | F | H | CH$_3$ | H | H |
| N | H | H | F | H | CF$_3$ | H | H |
| N | H | H | F | H | OCH$_3$ | H | H |
| N | H | H | F | H | H | F | H |
| N | H | H | F | H | H | H | F |
| N | H | H | F | H | H | H | Cl |
| N | H | H | F | H | H | H | CH$_3$ |
| N | H | H | F | H | H | H | CF$_3$ |
| N | H | H | F | H | H | H | OCH$_3$ |
| N | H | H | Cl | H | H | H | H |
| N | H | H | Cl | F | H | H | H |
| N | H | H | Cl | H | F | H | H |
| N | H | H | Cl | H | Cl | H | H |
| N | H | H | Cl | H | CH$_3$ | H | H |
| N | H | H | Cl | H | CF$_3$ | H | H |
| N | H | H | Cl | H | OCH$_3$ | H | H |
| N | H | H | Cl | H | H | F | H |
| N | H | H | Cl | H | H | H | F |
| N | H | H | Cl | H | H | H | Cl |
| N | H | H | Cl | H | H | H | CH$_3$ |
| N | H | H | Cl | H | H | H | CF$_3$ |
| N | H | H | Cl | H | H | H | OCH$_3$ |
| O | H | H | H | H | H | H | H |
| O | H | H | H | F | H | H | H |
| O | H | H | H | H | F | H | H |
| O | H | H | H | H | Cl | H | H |
| O | H | H | H | H | CH$_3$ | H | H |
| O | H | H | H | H | CF$_3$ | H | H |
| O | H | H | H | H | OCH$_3$ | H | H |
| O | H | H | H | H | H | F | H |
| O | H | H | H | H | H | H | F |
| O | H | H | H | H | H | H | Cl |
| O | H | H | H | H | H | H | CH$_3$ |
| O | H | H | H | H | H | H | CF$_3$ |
| O | H | H | H | H | H | H | OCH$_3$ |
| O | F | H | H | H | H | H | H |
| O | F | H | H | F | H | H | H |
| O | F | H | H | H | F | H | H |
| O | F | H | H | H | Cl | H | H |
| O | F | H | H | H | CH$_3$ | H | H |
| O | F | H | H | H | CF$_3$ | H | H |
| O | F | H | H | H | OCH$_3$ | H | H |
| O | F | H | H | H | H | F | H |
| O | F | H | H | H | H | H | F |
| O | F | H | H | H | H | H | Cl |
| O | F | H | H | H | H | H | CH$_3$ |
| O | F | H | H | H | H | H | CF$_3$ |
| O | F | H | H | H | H | H | OCH$_3$ |
| O | Cl | H | H | H | H | H | H |
| O | Cl | H | H | F | H | H | H |
| O | Cl | H | H | H | F | H | H |
| O | Cl | H | H | H | Cl | H | H |
| O | Cl | H | H | H | CH$_3$ | H | H |
| O | Cl | H | H | H | CF$_3$ | H | H |
| O | Cl | H | H | H | OCH$_3$ | H | H |
| O | Cl | H | H | H | H | F | H |
| O | Cl | H | H | H | H | H | F |
| O | Cl | H | H | H | H | H | Cl |
| O | Cl | H | H | H | H | H | CH$_3$ |
| O | Cl | H | H | H | H | H | CF$_3$ |
| O | Cl | H | H | H | H | H | OCH$_3$ |
| O | H | F | H | H | H | H | H |
| O | H | F | H | F | H | H | H |

TABLE 2-continued

| X | $R_{11}$ | $R_{12}$ | $R_{13}$ | $R_2^I$ | $R_3^I$ | $R_4^I$ | $R_5^I$ |
|---|---|---|---|---|---|---|---|
| O | H | F | H | H | F | H | H |
| O | H | F | H | H | Cl | H | H |
| O | H | F | H | H | $CH_3$ | H | H |
| O | H | F | H | H | $CF_3$ | H | H |
| O | H | F | H | H | $OCH_3$ | H | H |
| O | H | F | H | H | H | F | H |
| O | H | F | H | H | H | H | F |
| O | H | F | H | H | H | H | Cl |
| O | H | F | H | H | H | H | $CH_3$ |
| O | H | F | H | H | H | H | $CF_3$ |
| O | H | F | H | H | H | H | $OCH_3$ |
| O | H | Cl | H | H | H | H | H |
| O | H | Cl | H | F | H | H | H |
| O | H | Cl | H | H | F | H | H |
| O | H | Cl | H | H | Cl | H | H |
| O | H | Cl | H | H | $CH_3$ | H | H |
| O | H | Cl | H | H | $CF_3$ | H | H |
| O | H | Cl | H | H | $OCH_3$ | H | H |
| O | H | Cl | H | H | H | F | H |
| O | H | Cl | H | H | H | H | F |
| O | H | Cl | H | H | H | H | Cl |
| O | H | Cl | H | H | H | H | $CH_3$ |
| O | H | Cl | H | H | H | H | $CF_3$ |
| O | H | Cl | H | H | H | H | $OCH_3$ |
| O | H | H | F | H | H | H | H |
| O | H | H | F | F | H | H | H |
| O | H | H | F | H | F | H | H |
| O | H | H | F | H | Cl | H | H |
| O | H | H | F | H | $CH_3$ | H | H |
| O | H | H | F | H | $CF_3$ | H | H |
| O | H | H | F | H | $OCH_3$ | H | H |
| O | H | H | F | H | H | F | H |
| O | H | H | F | H | H | H | F |
| O | H | H | F | H | H | H | Cl |
| O | H | H | F | H | H | H | $CH_3$ |
| O | H | H | F | H | H | H | $CF_3$ |
| O | H | H | F | H | H | H | $OCH_3$ |
| O | H | H | Cl | H | H | H | H |
| O | H | H | Cl | F | H | H | H |
| O | H | H | Cl | H | F | H | H |
| O | H | H | Cl | H | Cl | H | H |
| O | H | H | Cl | H | $CH_3$ | H | H |
| O | H | H | Cl | H | $CF_3$ | H | H |
| O | H | H | Cl | H | $OCH_3$ | H | H |
| O | H | H | Cl | H | H | F | H |
| O | H | H | Cl | H | H | H | F |
| O | H | H | Cl | H | H | H | Cl |
| O | H | H | Cl | H | H | H | $CH_3$ |
| O | H | H | Cl | H | H | H | $CF_3$ |
| O | H | H | Cl | H | H | H | $OCH_3$ |

Preferably, the compound of formula (Ic)

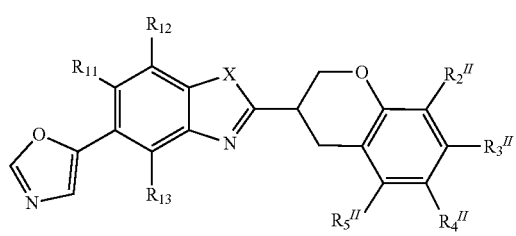

(Ic)

is selected from the group consisting of compounds of the formula (I), wherein X, $R_{11}$, $R_{12}$, $R_{13}$, $R_2^{II}$, $R_3^{II}$, $R_4^{II}$ and $R_5^{II}$ are as indicated in Table 3:

TABLE 3

| X | $R_{11}$ | $R_{12}$ | $R_{13}$ | $R_2^{II}$ | $R_3^{II}$ | $R_4^{II}$ | $R_5^{II}$ |
|---|---|---|---|---|---|---|---|
| N | H | H | H | H | H | H | H |
| N | H | H | H | F | H | H | H |
| N | H | H | H | H | F | H | H |
| N | H | H | H | H | Cl | H | H |
| N | H | H | H | H | $CH_3$ | H | H |
| N | H | H | H | H | $CF_3$ | H | H |
| N | H | H | H | H | $OCH_3$ | H | H |
| N | H | H | H | H | H | F | H |
| N | H | H | H | H | H | H | F |
| N | H | H | H | H | H | H | Cl |
| N | H | H | H | H | H | H | $CH_3$ |
| N | H | H | H | H | H | H | $CF_3$ |
| N | H | H | H | H | H | H | $OCH_3$ |
| N | F | H | H | H | H | H | H |
| N | F | H | H | F | H | H | H |
| N | F | H | H | H | F | H | H |
| N | F | H | H | H | Cl | H | H |
| N | F | H | H | H | $CH_3$ | H | H |
| N | F | H | H | H | $CF_3$ | H | H |
| N | F | H | H | H | $OCH_3$ | H | H |
| N | F | H | H | H | H | F | H |
| N | F | H | H | H | H | H | F |
| N | F | H | H | H | H | H | Cl |
| N | F | H | H | H | H | H | $CH_3$ |
| N | F | H | H | H | H | H | $CF_3$ |
| N | F | H | H | H | H | H | $OCH_3$ |
| N | Cl | H | H | H | H | H | H |
| N | Cl | H | H | F | H | H | H |
| N | Cl | H | H | H | F | H | H |
| N | Cl | H | H | H | Cl | H | H |
| N | Cl | H | H | H | $CH_3$ | H | H |
| N | Cl | H | H | H | $CF_3$ | H | H |
| N | Cl | H | H | H | $OCH_3$ | H | H |
| N | Cl | H | H | H | H | F | H |
| N | Cl | H | H | H | H | H | F |
| N | Cl | H | H | H | H | H | Cl |
| N | Cl | H | H | H | H | H | $CH_3$ |
| N | Cl | H | H | H | H | H | $CF_3$ |
| N | Cl | H | H | H | H | H | $OCH_3$ |
| N | H | F | H | H | H | H | H |
| N | H | F | H | F | H | H | H |
| N | H | F | H | H | F | H | H |
| N | H | F | H | H | Cl | H | H |
| N | H | F | H | H | $CH_3$ | H | H |
| N | H | F | H | H | $CF_3$ | H | H |
| N | H | F | H | H | $OCH_3$ | H | H |
| N | H | F | H | H | H | F | H |
| N | H | F | H | H | H | H | F |
| N | H | F | H | H | H | H | Cl |
| N | H | F | H | H | H | H | $CH_3$ |
| N | H | F | H | H | H | H | $CF_3$ |
| N | H | F | H | H | H | H | $OCH_3$ |
| N | H | Cl | H | H | H | H | H |
| N | H | Cl | H | F | H | H | H |
| N | H | Cl | H | H | F | H | H |
| N | H | Cl | H | H | Cl | H | H |
| N | H | Cl | H | H | $CH_3$ | H | H |
| N | H | Cl | H | H | $CF_3$ | H | H |
| N | H | Cl | H | H | $OCH_3$ | H | H |
| N | H | Cl | H | H | H | F | H |
| N | H | Cl | H | H | H | H | F |
| N | H | Cl | H | H | H | H | Cl |
| N | H | Cl | H | H | H | H | $CH_3$ |
| N | H | Cl | H | H | H | H | $CF_3$ |
| N | H | Cl | H | H | H | H | $OCH_3$ |
| N | H | H | F | H | H | H | H |
| N | H | H | F | F | H | H | H |
| N | H | H | F | H | F | H | H |
| N | H | H | F | H | Cl | H | H |
| N | H | H | F | H | $CH_3$ | H | H |
| N | H | H | F | H | $CF_3$ | H | H |
| N | H | H | F | H | $OCH_3$ | H | H |
| N | H | H | F | H | H | F | H |
| N | H | H | F | H | H | H | F |
| N | H | H | F | H | H | H | Cl |
| N | H | H | F | H | H | H | $CH_3$ |
| N | H | H | F | H | H | H | $CF_3$ |
| N | H | H | F | H | H | H | $OCH_3$ |

TABLE 3-continued

| X | $R_{11}$ | $R_{12}$ | $R_{13}$ | $R_2^{II}$ | $R_3^{II}$ | $R_4^{II}$ | $R_5^{II}$ |
|---|---|---|---|---|---|---|---|
| N | H | H | Cl | H | H | H | H |
| N | H | H | Cl | F | H | H | H |
| N | H | H | Cl | H | F | H | H |
| N | H | H | Cl | H | Cl | H | H |
| N | H | H | Cl | H | $CH_3$ | H | H |
| N | H | H | Cl | H | $CF_3$ | H | H |
| N | H | H | Cl | H | $OCH_3$ | H | H |
| N | H | H | Cl | H | H | F | H |
| N | H | H | Cl | H | H | H | F |
| N | H | H | Cl | H | H | H | Cl |
| N | H | H | Cl | H | H | H | $CH_3$ |
| N | H | H | Cl | H | H | H | $CF_3$ |
| N | H | H | Cl | H | H | H | $OCH_3$ |
| O | H | H | H | H | H | H | H |
| O | H | H | H | F | H | H | H |
| O | H | H | H | H | F | H | H |
| O | H | H | H | H | Cl | H | H |
| O | H | H | H | H | $CH_3$ | H | H |
| O | H | H | H | H | $CF_3$ | H | H |
| O | H | H | H | H | $OCH_3$ | H | H |
| O | H | H | H | H | H | F | H |
| O | H | H | H | H | H | H | F |
| O | H | H | H | H | H | H | Cl |
| O | H | H | H | H | H | H | $CH_3$ |
| O | H | H | H | H | H | H | $CF_3$ |
| O | H | H | H | H | H | H | $OCH_3$ |
| O | F | H | H | H | H | H | H |
| O | F | H | H | F | H | H | H |
| O | F | H | H | H | F | H | H |
| O | F | H | H | H | Cl | H | H |
| O | F | H | H | H | $CH_3$ | H | H |
| O | F | H | H | H | $CF_3$ | H | H |
| O | F | H | H | H | $OCH_3$ | H | H |
| O | F | H | H | H | H | F | H |
| O | F | H | H | H | H | H | F |
| O | F | H | H | H | H | H | Cl |
| O | F | H | H | H | H | H | $CH_3$ |
| O | F | H | H | H | H | H | $CF_3$ |
| O | F | H | H | H | H | H | $OCH_3$ |
| O | Cl | H | H | H | H | H | H |
| O | Cl | H | H | F | H | H | H |
| O | Cl | H | H | H | F | H | H |
| O | Cl | H | H | H | Cl | H | H |
| O | Cl | H | H | H | $CH_3$ | H | H |
| O | Cl | H | H | H | $CF_3$ | H | H |
| O | Cl | H | H | H | $OCH_3$ | H | H |
| O | Cl | H | H | H | H | F | H |
| O | Cl | H | H | H | H | H | F |
| O | Cl | H | H | H | H | H | Cl |
| O | Cl | H | H | H | H | H | $CH_3$ |
| O | Cl | H | H | H | H | H | $CF_3$ |
| O | Cl | H | H | H | H | H | $OCH_3$ |
| O | H | F | H | H | H | H | H |
| O | H | F | H | F | H | H | H |
| O | H | F | H | H | F | H | H |
| O | H | F | H | H | Cl | H | H |
| O | H | F | H | H | $CH_3$ | H | H |
| O | H | F | H | H | $CF_3$ | H | H |
| O | H | F | H | H | $OCH_3$ | H | H |
| O | H | F | H | H | H | F | H |
| O | H | F | H | H | H | H | F |
| O | H | F | H | H | H | H | Cl |
| O | H | F | H | H | H | H | $CH_3$ |
| O | H | F | H | H | H | H | $CF_3$ |
| O | H | F | H | H | H | H | $OCH_3$ |
| O | H | Cl | H | H | H | H | H |
| O | H | Cl | H | F | H | H | H |
| O | H | Cl | H | H | F | H | H |
| O | H | Cl | H | H | Cl | H | H |
| O | H | Cl | H | H | $CH_3$ | H | H |
| O | H | Cl | H | H | $CF_3$ | H | H |
| O | H | Cl | H | H | $OCH_3$ | H | H |
| O | H | Cl | H | H | H | F | H |
| O | H | Cl | H | H | H | H | F |
| O | H | Cl | H | H | H | H | Cl |
| O | H | Cl | H | H | H | H | $CH_3$ |
| O | H | Cl | H | H | H | H | $CF_3$ |
| O | H | Cl | H | H | H | H | $OCH_3$ |
| O | H | H | F | H | H | H | H |
| O | H | H | F | F | H | H | H |
| O | H | H | F | H | F | H | H |
| O | H | H | F | H | Cl | H | H |
| O | H | H | F | H | $CH_3$ | H | H |
| O | H | H | F | H | $CF_3$ | H | H |
| O | H | H | F | H | $OCH_3$ | H | H |
| O | H | H | F | H | H | F | H |
| O | H | H | F | H | H | H | F |
| O | H | H | F | H | H | H | Cl |
| O | H | H | F | H | H | H | $CH_3$ |
| O | H | H | F | H | H | H | $CF_3$ |
| O | H | H | F | H | H | H | $OCH_3$ |
| O | H | H | Cl | H | H | H | H |
| O | H | H | Cl | F | H | H | H |
| O | H | H | Cl | H | F | H | H |
| O | H | H | Cl | H | Cl | H | H |
| O | H | H | Cl | H | $CH_3$ | H | H |
| O | H | H | Cl | H | $CF_3$ | H | H |
| O | H | H | Cl | H | $OCH_3$ | H | H |
| O | H | H | Cl | H | H | F | H |
| O | H | H | Cl | H | H | H | F |
| O | H | H | Cl | H | H | H | Cl |
| O | H | H | Cl | H | H | H | $CH_3$ |
| O | H | H | Cl | H | H | H | $CF_3$ |
| O | H | H | Cl | H | H | H | $OCH_3$ |

Preferably, the compound of formula (Id)

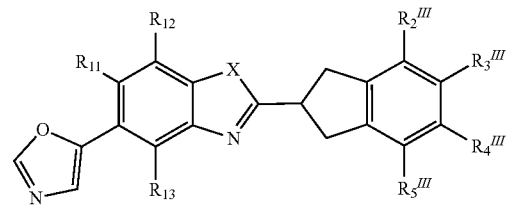

is selected from the group consisting of compounds of the formula (I), wherein $R_{11}$, $R_{12}$, $R_{13}$, $R_2^{III}$, $R_3^{III}$, $R_4^{III}$, $R_5^{III}$ are as indicated in Table 4:

TABLE 4

| X | $R_{11}$ | $R_{12}$ | $R_{13}$ | $R_2^{III}$ | $R_3^{III}$ | $R_4^{III}$ | $R_5^{III}$ |
|---|---|---|---|---|---|---|---|
| N | H | H | H | H | H | H | H |
| N | H | H | H | F | H | H | H |
| N | H | H | H | H | F | H | H |
| N | H | H | H | H | Cl | H | H |
| N | H | H | H | H | $CH_3$ | H | H |
| N | H | H | H | H | $CF_3$ | H | H |
| N | H | H | H | H | $OCH_3$ | H | H |
| N | H | H | H | H | H | F | H |
| N | H | H | H | H | H | H | F |
| N | H | H | H | H | H | H | Cl |
| N | H | H | H | H | H | H | $CH_3$ |
| N | H | H | H | H | H | H | $CF_3$ |
| N | H | H | H | H | H | H | $OCH_3$ |
| N | F | H | H | H | H | H | H |
| N | F | H | H | F | H | H | H |
| N | F | H | H | H | F | H | H |
| N | F | H | H | H | Cl | H | H |
| N | F | H | H | H | $CH_3$ | H | H |
| N | F | H | H | H | $CF_3$ | H | H |
| N | F | H | H | H | $OCH_3$ | H | H |
| N | F | H | H | H | H | F | H |
| N | F | H | H | H | H | H | F |
| N | F | H | H | H | H | H | Cl |
| N | F | H | H | H | H | H | $CH_3$ |

TABLE 4-continued

| X | $R_{11}$ | $R_{12}$ | $R_{13}$ | $R_2^{III}$ | $R_3^{III}$ | $R_4^{III}$ | $R_5^{III}$ |
|---|---|---|---|---|---|---|---|
| N | F | H | H | H | H | H | $CF_3$ |
| N | F | H | H | H | H | H | $OCH_3$ |
| N | Cl | H | H | H | H | H | H |
| N | Cl | H | H | F | H | H | H |
| N | Cl | H | H | H | F | H | H |
| N | Cl | H | H | H | Cl | H | H |
| N | Cl | H | H | H | $CH_3$ | H | H |
| N | Cl | H | H | H | $CF_3$ | H | H |
| N | Cl | H | H | H | $OCH_3$ | H | H |
| N | Cl | H | H | H | H | F | H |
| N | Cl | H | H | H | H | H | F |
| N | Cl | H | H | H | H | H | Cl |
| N | Cl | H | H | H | H | H | $CH_3$ |
| N | Cl | H | H | H | H | H | $CF_3$ |
| N | Cl | H | H | H | H | H | $OCH_3$ |
| N | H | F | H | H | H | H | H |
| N | H | F | H | F | H | H | H |
| N | H | F | H | H | F | H | H |
| N | H | F | H | H | Cl | H | H |
| N | H | F | H | H | $CH_3$ | H | H |
| N | H | F | H | H | $CF_3$ | H | H |
| N | H | F | H | H | $OCH_3$ | H | H |
| N | H | F | H | H | H | F | H |
| N | H | F | H | H | H | H | F |
| N | H | F | H | H | H | H | Cl |
| N | H | F | H | H | H | H | $CH_3$ |
| N | H | F | H | H | H | H | $CF_3$ |
| N | H | F | H | H | H | H | $OCH_3$ |
| N | H | Cl | H | H | H | H | H |
| N | H | Cl | H | F | H | H | H |
| N | H | Cl | H | H | F | H | H |
| N | H | Cl | H | H | Cl | H | H |
| N | H | Cl | H | H | $CH_3$ | H | H |
| N | H | Cl | H | H | $CF_3$ | H | H |
| N | H | Cl | H | H | $OCH_3$ | H | H |
| N | H | Cl | H | H | H | F | H |
| N | H | Cl | H | H | H | H | F |
| N | H | Cl | H | H | H | H | Cl |
| N | H | Cl | H | H | H | H | $CH_3$ |
| N | H | Cl | H | H | H | H | $CF_3$ |
| N | H | Cl | H | H | H | H | $OCH_3$ |
| N | H | H | F | H | H | H | H |
| N | H | H | F | F | H | H | H |
| N | H | H | F | H | F | H | H |
| N | H | H | F | H | Cl | H | H |
| N | H | H | F | H | $CH_3$ | H | H |
| N | H | H | F | H | $CF_3$ | H | H |
| N | H | H | F | H | $OCH_3$ | H | H |
| N | H | H | F | H | H | F | H |
| N | H | H | F | H | H | H | F |
| N | H | H | F | H | H | H | Cl |
| N | H | H | F | H | H | H | $CH_3$ |
| N | H | H | F | H | H | H | $CF_3$ |
| N | H | H | F | H | H | H | $OCH_3$ |
| N | H | H | Cl | H | H | H | H |
| N | H | H | Cl | F | H | H | H |
| N | H | H | Cl | H | F | H | H |
| N | H | H | Cl | H | Cl | H | H |
| N | H | H | Cl | H | $CH_3$ | H | H |
| N | H | H | Cl | H | $CF_3$ | H | H |
| N | H | H | Cl | H | $OCH_3$ | H | H |
| N | H | H | Cl | H | H | F | H |
| N | H | H | Cl | H | H | H | F |
| N | H | H | Cl | H | H | H | Cl |
| N | H | H | Cl | H | H | H | $CH_3$ |
| N | H | H | Cl | H | H | H | $CF_3$ |
| N | H | H | Cl | H | H | H | $OCH_3$ |
| O | H | H | H | H | H | H | H |
| O | H | H | H | F | H | H | H |
| O | H | H | H | H | F | H | H |
| O | H | H | H | H | Cl | H | H |
| O | H | H | H | H | $CH_3$ | H | H |
| O | H | H | H | H | $CF_3$ | H | H |
| O | H | H | H | H | $OCH_3$ | H | H |
| O | H | H | H | H | H | F | H |
| O | H | H | H | H | H | H | F |
| O | H | H | H | H | H | H | Cl |
| O | H | H | H | H | H | H | $CH_3$ |
| O | H | H | H | H | H | H | $CF_3$ |
| O | H | H | H | H | H | H | $OCH_3$ |
| O | F | H | H | H | H | H | H |
| O | F | H | H | F | H | H | H |
| O | F | H | H | H | F | H | H |
| O | F | H | H | H | Cl | H | H |
| O | F | H | H | H | $CH_3$ | H | H |
| O | F | H | H | H | $CF_3$ | H | H |
| O | F | H | H | H | $OCH_3$ | H | H |
| O | F | H | H | H | H | F | H |
| O | F | H | H | H | H | H | F |
| O | F | H | H | H | H | H | Cl |
| O | F | H | H | H | H | H | $CH_3$ |
| O | F | H | H | H | H | H | $CF_3$ |
| O | F | H | H | H | H | H | $OCH_3$ |
| O | Cl | H | H | H | H | H | H |
| O | Cl | H | H | F | H | H | H |
| O | Cl | H | H | H | F | H | H |
| O | Cl | H | H | H | Cl | H | H |
| O | Cl | H | H | H | $CH_3$ | H | H |
| O | Cl | H | H | H | $CF_3$ | H | H |
| O | Cl | H | H | H | $OCH_3$ | H | H |
| O | Cl | H | H | H | H | F | H |
| O | Cl | H | H | H | H | H | F |
| O | Cl | H | H | H | H | H | Cl |
| O | Cl | H | H | H | H | H | $CH_3$ |
| O | Cl | H | H | H | H | H | $CF_3$ |
| O | Cl | H | H | H | H | H | $OCH_3$ |
| O | H | F | H | H | H | H | H |
| O | H | F | H | F | H | H | H |
| O | H | F | H | H | F | H | H |
| O | H | F | H | H | Cl | H | H |
| O | H | F | H | H | $CH_3$ | H | H |
| O | H | F | H | H | $CF_3$ | H | H |
| O | H | F | H | H | $OCH_3$ | H | H |
| O | H | F | H | H | H | F | H |
| O | H | F | H | H | H | H | F |
| O | H | F | H | H | H | H | Cl |
| O | H | F | H | H | H | H | $CH_3$ |
| O | H | F | H | H | H | H | $CF_3$ |
| O | H | F | H | H | H | H | $OCH_3$ |
| O | H | Cl | H | H | H | H | H |
| O | H | Cl | H | F | H | H | H |
| O | H | Cl | H | H | F | H | H |
| O | H | Cl | H | H | Cl | H | H |
| O | H | Cl | H | H | $CH_3$ | H | H |
| O | H | Cl | H | H | $CF_3$ | H | H |
| O | H | Cl | H | H | $OCH_3$ | H | H |
| O | H | Cl | H | H | H | F | H |
| O | H | Cl | H | H | H | H | F |
| O | H | Cl | H | H | H | H | Cl |
| O | H | Cl | H | H | H | H | $CH_3$ |
| O | H | Cl | H | H | H | H | $CF_3$ |
| O | H | Cl | H | H | H | H | $OCH_3$ |
| O | H | H | F | H | H | H | H |
| O | H | H | F | F | H | H | H |
| O | H | H | F | H | F | H | H |
| O | H | H | F | H | Cl | H | H |
| O | H | H | F | H | $CH_3$ | H | H |
| O | H | H | F | H | $CF_3$ | H | H |
| O | H | H | F | H | $OCH_3$ | H | H |
| O | H | H | F | H | H | F | H |
| O | H | H | F | H | H | H | F |
| O | H | H | F | H | H | H | Cl |
| O | H | H | F | H | H | H | $CH_3$ |
| O | H | H | F | H | H | H | $CF_3$ |
| O | H | H | F | H | H | H | $OCH_3$ |
| O | H | H | Cl | H | H | H | H |
| O | H | H | Cl | F | H | H | H |
| O | H | H | Cl | H | F | H | H |
| O | H | H | Cl | H | Cl | H | H |
| O | H | H | Cl | H | $CH_3$ | H | H |
| O | H | H | Cl | H | $CF_3$ | H | H |
| O | H | H | Cl | H | $OCH_3$ | H | H |
| O | H | H | Cl | H | H | F | H |
| O | H | H | Cl | H | H | H | F |
| O | H | H | Cl | H | H | H | Cl |
| O | H | H | Cl | H | H | H | $CH_3$ |

TABLE 4-continued

| X | $R_{11}$ | $R_{12}$ | $R_{13}$ | $R_2^{III}$ | $R_3^{III}$ | $R_4^{III}$ | $R_5^{III}$ |
|---|---|---|---|---|---|---|---|
| O | H | H | Cl | H | H | H | $CF_3$ |
| O | H | H | Cl | H | H | H | $OCH_3$ |

Preferably, the compound of formula (Ie)

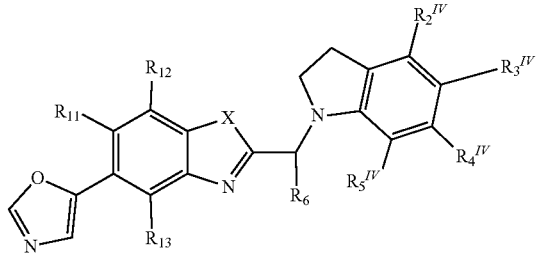

(Ie)

is selected from the group consisting of compounds of the formula (I), wherein $R_{11}$, $R_{12}$, $R_{13}$, $R_2^{VI}$, $R_3^{IV}$, $R_4^{IV}$, $R_5^{IV}$ and $R_6$ are as indicated in Table 5:

TABLE 5

| X | $R_{11}$ | $R_{12}$ | $R_{13}$ | $R_2^{IV}$ | $R_3^{IV}$ | $R_4^{IV}$ | $R_5^{IV}$ | $R_6$ |
|---|---|---|---|---|---|---|---|---|
| N | H | H | H | H | H | H | H | $CH_3$ |
| N | H | H | H | F | H | H | H | $CH_3$ |
| N | H | H | H | H | F | H | H | $CH_3$ |
| N | H | H | H | H | Cl | H | H | $CH_3$ |
| N | H | H | H | H | $CH_3$ | H | H | $CH_3$ |
| N | H | H | H | H | $CF_3$ | H | H | $CH_3$ |
| N | H | H | H | H | $OCH_3$ | H | H | $CH_3$ |
| N | H | H | H | H | H | F | H | $CH_3$ |
| N | H | H | H | H | H | H | F | $CH_3$ |
| N | H | H | H | H | H | H | Cl | $CH_3$ |
| N | H | H | H | H | H | H | $CH_3$ | $CH_3$ |
| N | H | H | H | H | H | H | $CF_3$ | $CH_3$ |
| N | H | H | H | H | H | H | $OCH_3$ | $CH_3$ |
| N | F | H | H | H | H | H | H | $CH_3$ |
| N | F | H | H | F | H | H | H | $CH_3$ |
| N | F | H | H | H | F | H | H | $CH_3$ |
| N | F | H | H | H | Cl | H | H | $CH_3$ |
| N | F | H | H | H | $CH_3$ | H | H | $CH_3$ |
| N | F | H | H | H | $CF_3$ | H | H | $CH_3$ |
| N | F | H | H | H | $OCH_3$ | H | H | $CH_3$ |
| N | F | H | H | H | H | F | H | $CH_3$ |
| N | F | H | H | H | H | H | F | $CH_3$ |
| N | F | H | H | H | H | H | Cl | $CH_3$ |
| N | F | H | H | H | H | H | $CH_3$ | $CH_3$ |
| N | F | H | H | H | H | H | $CF_3$ | $CH_3$ |
| N | F | H | H | H | H | H | $OCH_3$ | $CH_3$ |
| N | Cl | H | H | H | H | H | H | $CH_3$ |
| N | Cl | H | H | F | H | H | H | $CH_3$ |
| N | Cl | H | H | H | F | H | H | $CH_3$ |
| N | Cl | H | H | H | Cl | H | H | $CH_3$ |
| N | Cl | H | H | H | $CH_3$ | H | H | $CH_3$ |
| N | Cl | H | H | H | $CF_3$ | H | H | $CH_3$ |
| N | Cl | H | H | H | $OCH_3$ | H | H | $CH_3$ |
| N | Cl | H | H | H | H | F | H | $CH_3$ |
| N | Cl | H | H | H | H | H | F | $CH_3$ |
| N | Cl | H | H | H | H | H | Cl | $CH_3$ |
| N | Cl | H | H | H | H | H | $CH_3$ | $CH_3$ |
| N | Cl | H | H | H | H | H | $CF_3$ | $CH_3$ |
| N | Cl | H | H | H | H | H | $OCH_3$ | $CH_3$ |
| N | H | F | H | H | H | H | H | $CH_3$ |
| N | H | F | H | F | H | H | H | $CH_3$ |
| N | H | F | H | H | F | H | H | $CH_3$ |
| N | H | F | H | H | Cl | H | H | $CH_3$ |
| N | H | F | H | H | $CH_3$ | H | H | $CH_3$ |
| N | H | F | H | H | $CF_3$ | H | H | $CH_3$ |
| N | H | F | H | H | $OCH_3$ | H | H | $CH_3$ |
| N | H | F | H | H | H | F | H | $CH_3$ |
| N | H | F | H | H | H | H | F | $CH_3$ |
| N | H | F | H | H | H | H | Cl | $CH_3$ |
| N | H | F | H | H | H | H | $CH_3$ | $CH_3$ |
| N | H | F | H | H | H | H | $CF_3$ | $CH_3$ |
| N | H | F | H | H | H | H | $OCH_3$ | $CH_3$ |
| N | H | Cl | H | H | H | H | H | $CH_3$ |
| N | H | Cl | H | F | H | H | H | $CH_3$ |
| N | H | Cl | H | H | F | H | H | $CH_3$ |
| N | H | Cl | H | H | Cl | H | H | $CH_3$ |
| N | H | Cl | H | H | $CH_3$ | H | H | $CH_3$ |
| N | H | Cl | H | H | $CF_3$ | H | H | $CH_3$ |
| N | H | Cl | H | H | $OCH_3$ | H | H | $CH_3$ |
| N | H | Cl | H | H | H | F | H | $CH_3$ |
| N | H | Cl | H | H | H | H | F | $CH_3$ |
| N | H | Cl | H | H | H | H | Cl | $CH_3$ |
| N | H | Cl | H | H | H | H | $CH_3$ | $CH_3$ |
| N | H | Cl | H | H | H | H | $CF_3$ | $CH_3$ |
| N | H | Cl | H | H | H | H | $OCH_3$ | $CH_3$ |
| N | H | H | F | H | H | H | H | $CH_3$ |
| N | H | H | F | F | H | H | H | $CH_3$ |
| N | H | H | F | H | F | H | H | $CH_3$ |
| N | H | H | F | H | Cl | H | H | $CH_3$ |
| N | H | H | F | H | $CH_3$ | H | H | $CH_3$ |
| N | H | H | F | H | $CF_3$ | H | H | $CH_3$ |
| N | H | H | F | H | $OCH_3$ | H | H | $CH_3$ |
| N | H | H | F | H | H | F | H | $CH_3$ |
| N | H | H | F | H | H | H | F | $CH_3$ |
| N | H | H | F | H | H | H | Cl | $CH_3$ |
| N | H | H | F | H | H | H | $CH_3$ | $CH_3$ |
| N | H | H | F | H | H | H | $CF_3$ | $CH_3$ |
| N | H | H | F | H | H | H | $OCH_3$ | $CH_3$ |
| N | H | H | Cl | H | H | H | H | $CH_3$ |
| N | H | H | Cl | F | H | H | H | $CH_3$ |
| N | H | H | Cl | H | F | H | H | $CH_3$ |
| N | H | H | Cl | H | Cl | H | H | $CH_3$ |
| N | H | H | Cl | H | $CH_3$ | H | H | $CH_3$ |
| N | H | H | Cl | H | $CF_3$ | H | H | $CH_3$ |
| N | H | H | Cl | H | $OCH_3$ | H | H | $CH_3$ |
| N | H | H | Cl | H | H | F | H | $CH_3$ |
| N | H | H | Cl | H | H | H | F | $CH_3$ |
| N | H | H | Cl | H | H | H | Cl | $CH_3$ |
| N | H | H | Cl | H | H | H | $CH_3$ | $CH_3$ |
| N | H | H | Cl | H | H | H | $CF_3$ | $CH_3$ |
| N | H | H | Cl | H | H | H | $OCH_3$ | $CH_3$ |
| O | H | H | H | H | H | H | H | $CH_3$ |
| O | H | H | H | F | H | H | H | $CH_3$ |
| O | H | H | H | H | F | H | H | $CH_3$ |
| O | H | H | H | H | Cl | H | H | $CH_3$ |
| O | H | H | H | H | $CH_3$ | H | H | $CH_3$ |
| O | H | H | H | H | $CF_3$ | H | H | $CH_3$ |
| O | H | H | H | H | $OCH_3$ | H | H | $CH_3$ |
| O | H | H | H | H | H | F | H | $CH_3$ |
| O | H | H | H | H | H | H | F | $CH_3$ |
| O | H | H | H | H | H | H | Cl | $CH_3$ |
| O | H | H | H | H | H | H | $CH_3$ | $CH_3$ |
| O | H | H | H | H | H | H | $CF_3$ | $CH_3$ |
| O | H | H | H | H | H | H | $OCH_3$ | $CH_3$ |
| O | F | H | H | H | H | H | H | $CH_3$ |
| O | F | H | H | F | H | H | H | $CH_3$ |
| O | F | H | H | H | F | H | H | $CH_3$ |
| O | F | H | H | H | Cl | H | H | $CH_3$ |
| O | F | H | H | H | $CH_3$ | H | H | $CH_3$ |
| O | F | H | H | H | $CF_3$ | H | H | $CH_3$ |
| O | F | H | H | H | $OCH_3$ | H | H | $CH_3$ |
| O | F | H | H | H | H | F | H | $CH_3$ |
| O | F | H | H | H | H | H | F | $CH_3$ |
| O | F | H | H | H | H | H | Cl | $CH_3$ |
| O | F | H | H | H | H | H | $CH_3$ | $CH_3$ |
| O | F | H | H | H | H | H | $CF_3$ | $CH_3$ |
| O | F | H | H | H | H | H | $OCH_3$ | $CH_3$ |
| O | Cl | H | H | H | H | H | H | $CH_3$ |
| O | Cl | H | H | F | H | H | H | $CH_3$ |
| O | Cl | H | H | H | F | H | H | $CH_3$ |
| O | Cl | H | H | H | Cl | H | H | $CH_3$ |
| O | Cl | H | H | H | $CH_3$ | H | H | $CH_3$ |
| O | Cl | H | H | H | $CF_3$ | H | H | $CH_3$ |
| O | Cl | H | H | H | $OCH_3$ | H | H | $CH_3$ |

TABLE 5-continued

| X | $R_{11}$ | $R_{12}$ | $R_{13}$ | $R_2^{IV}$ | $R_3^{IV}$ | $R_4^{IV}$ | $R_5^{IV}$ | $R_6$ |
|---|---|---|---|---|---|---|---|---|
| O | Cl | H | H | H | H | F | H | $CH_3$ |
| O | Cl | H | H | H | H | H | F | $CH_3$ |
| O | Cl | H | H | H | H | H | Cl | $CH_3$ |
| O | Cl | H | H | H | H | H | $CH_3$ | $CH_3$ |
| O | Cl | H | H | H | H | H | $CF_3$ | $CH_3$ |
| O | Cl | H | H | H | H | H | $OCH_3$ | $CH_3$ |
| O | H | F | H | H | H | H | H | $CH_3$ |
| O | H | F | H | F | H | H | H | $CH_3$ |
| O | H | F | H | H | F | H | H | $CH_3$ |
| O | H | F | H | H | Cl | H | H | $CH_3$ |
| O | H | F | H | H | $CH_3$ | H | H | $CH_3$ |
| O | H | F | H | H | $CF_3$ | H | H | $CH_3$ |
| O | H | F | H | H | $OCH_3$ | H | H | $CH_3$ |
| O | H | F | H | H | H | F | H | $CH_3$ |
| O | H | F | H | H | H | H | F | $CH_3$ |
| O | H | F | H | H | H | H | Cl | $CH_3$ |
| O | H | F | H | H | H | H | $CH_3$ | $CH_3$ |
| O | H | F | H | H | H | H | $CF_3$ | $CH_3$ |
| O | H | F | H | H | H | H | $OCH_3$ | $CH_3$ |
| O | H | Cl | H | H | H | H | H | $CH_3$ |
| O | H | Cl | H | F | H | H | H | $CH_3$ |
| O | H | Cl | H | H | F | H | H | $CH_3$ |
| O | H | Cl | H | H | Cl | H | H | $CH_3$ |
| O | H | Cl | H | H | $CH_3$ | H | H | $CH_3$ |
| O | H | Cl | H | H | $CF_3$ | H | H | $CH_3$ |
| O | H | Cl | H | H | $OCH_3$ | H | H | $CH_3$ |
| O | H | Cl | H | H | H | F | H | $CH_3$ |
| O | H | Cl | H | H | H | H | F | $CH_3$ |
| O | H | Cl | H | H | H | H | Cl | $CH_3$ |
| O | H | Cl | H | H | H | H | $CH_3$ | $CH_3$ |
| O | H | Cl | H | H | H | H | $CF_3$ | $CH_3$ |
| O | H | Cl | H | H | H | H | $OCH_3$ | $CH_3$ |
| O | H | H | F | H | H | H | H | $CH_3$ |
| O | H | H | F | F | H | H | H | $CH_3$ |
| O | H | H | F | H | F | H | H | $CH_3$ |
| O | H | H | F | H | Cl | H | H | $CH_3$ |
| O | H | H | F | H | $CH_3$ | H | H | $CH_3$ |
| O | H | H | F | H | $CF_3$ | H | H | $CH_3$ |
| O | H | H | F | H | $OCH_3$ | H | H | $CH_3$ |
| O | H | H | F | H | H | F | H | $CH_3$ |
| O | H | H | F | H | H | H | F | $CH_3$ |
| O | H | H | F | H | H | H | Cl | $CH_3$ |
| O | H | H | F | H | H | H | $CH_3$ | $CH_3$ |
| O | H | H | F | H | H | H | $CF_3$ | $CH_3$ |
| O | H | H | F | H | H | H | $OCH_3$ | $CH_3$ |
| O | H | H | Cl | H | H | H | H | $CH_3$ |
| O | H | H | Cl | F | H | H | H | $CH_3$ |
| O | H | H | Cl | H | F | H | H | $CH_3$ |
| O | H | H | Cl | H | Cl | H | H | $CH_3$ |
| O | H | H | Cl | H | $CH_3$ | H | H | $CH_3$ |
| O | H | H | Cl | H | $CF_3$ | H | H | $CH_3$ |
| O | H | H | Cl | H | $OCH_3$ | H | H | $CH_3$ |
| O | H | H | Cl | H | H | F | H | $CH_3$ |
| O | H | H | Cl | H | H | H | F | $CH_3$ |
| O | H | H | Cl | H | H | H | Cl | $CH_3$ |
| O | H | H | Cl | H | H | H | $CH_3$ | $CH_3$ |
| O | H | H | Cl | H | H | H | $CF_3$ | $CH_3$ |
| O | H | H | Cl | H | H | H | $OCH_3$ | $CH_3$ |

Preferably, the compound of formula (If)

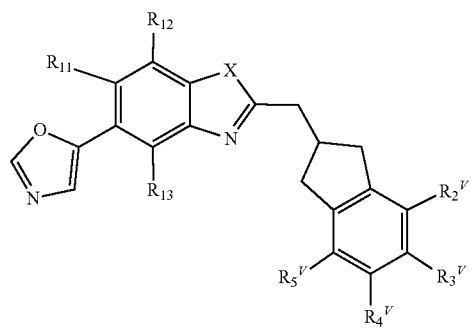

(If)

is selected from the group consisting of compounds of the formula (I), wherein $R_{11}$, $R_{12}$, $R_{13}$, $R_2^V$, $R_3^V$, $R_4^V$ and $R_5^V$ are as indicated in Table 6:

TABLE 6

| X | $R_{11}$ | $R_{12}$ | $R_{13}$ | $R_2^V$ | $R_3^V$ | $R_4^V$ | $R_5^V$ |
|---|---|---|---|---|---|---|---|
| N | H | H | H | H | H | H | H |
| N | H | H | H | F | H | H | H |
| N | H | H | H | H | F | H | H |
| N | H | H | H | H | Cl | H | H |
| N | H | H | H | H | $CH_3$ | H | H |
| N | H | H | H | H | $CF_3$ | H | H |
| N | H | H | H | H | $OCH_3$ | H | H |
| N | H | H | H | H | H | F | H |
| N | H | H | H | H | H | H | F |
| N | H | H | H | H | H | H | Cl |
| N | H | H | H | H | H | H | $CH_3$ |
| N | H | H | H | H | H | H | $CF_3$ |
| N | H | H | H | H | H | H | $OCH_3$ |
| N | F | H | H | H | H | H | H |
| N | F | H | H | F | H | H | H |
| N | F | H | H | H | F | H | H |
| N | F | H | H | H | Cl | H | H |
| N | F | H | H | H | $CH_3$ | H | H |
| N | F | H | H | H | $CF_3$ | H | H |
| N | F | H | H | H | $OCH_3$ | H | H |
| N | F | H | H | H | H | F | H |
| N | F | H | H | H | H | H | F |
| N | F | H | H | H | H | H | Cl |
| N | F | H | H | H | H | H | $CH_3$ |
| N | F | H | H | H | H | H | $CF_3$ |
| N | F | H | H | H | H | H | $OCH_3$ |
| N | Cl | H | H | H | H | H | H |
| N | Cl | H | H | F | H | H | H |
| N | Cl | H | H | H | F | H | H |
| N | Cl | H | H | H | Cl | H | H |
| N | Cl | H | H | H | $CH_3$ | H | H |
| N | Cl | H | H | H | $CF_3$ | H | H |
| N | Cl | H | H | H | $OCH_3$ | H | H |
| N | Cl | H | H | H | H | F | H |
| N | Cl | H | H | H | H | H | F |
| N | Cl | H | H | H | H | H | Cl |
| N | Cl | H | H | H | H | H | $CH_3$ |
| N | Cl | H | H | H | H | H | $CF_3$ |
| N | Cl | H | H | H | H | H | $OCH_3$ |
| N | H | F | H | H | H | H | H |
| N | H | F | H | F | H | H | H |
| N | H | F | H | H | F | H | H |
| N | H | F | H | H | Cl | H | H |
| N | H | F | H | H | $CH_3$ | H | H |
| N | H | F | H | H | $CF_3$ | H | H |
| N | H | F | H | H | $OCH_3$ | H | H |
| N | H | F | H | H | H | F | H |
| N | H | F | H | H | H | H | F |
| N | H | F | H | H | H | H | Cl |
| N | H | F | H | H | H | H | $CH_3$ |
| N | H | F | H | H | H | H | $CF_3$ |

TABLE 6-continued

| X | $R_{11}$ | $R_{12}$ | $R_{13}$ | $R_2^V$ | $R_3^V$ | $R_4^V$ | $R_5^V$ |
|---|---|---|---|---|---|---|---|
| N | H | F | H | H | H | H | OCH₃ |
| N | H | Cl | H | F | H | H | H |
| N | H | Cl | H | H | F | H | H |
| N | H | Cl | H | H | Cl | H | H |
| N | H | Cl | H | H | CH₃ | H | H |
| N | H | Cl | H | H | CF₃ | H | H |
| N | H | Cl | H | H | OCH₃ | H | H |
| N | H | Cl | H | H | H | F | H |
| N | H | Cl | H | H | H | H | F |
| N | H | Cl | H | H | H | H | Cl |
| N | H | Cl | H | H | H | H | CH₃ |
| N | H | Cl | H | H | H | H | CF₃ |
| N | H | Cl | H | H | H | H | OCH₃ |
| N | H | H | F | H | H | H | H |
| N | H | H | F | F | H | H | H |
| N | H | H | F | H | F | H | H |
| N | H | H | F | H | Cl | H | H |
| N | H | H | F | H | CH₃ | H | H |
| N | H | H | F | H | CF₃ | H | H |
| N | H | H | F | H | OCH₃ | H | H |
| N | H | H | F | H | H | F | H |
| N | H | H | F | H | H | H | F |
| N | H | H | F | H | H | H | Cl |
| N | H | H | F | H | H | H | CH₃ |
| N | H | H | F | H | H | H | CF₃ |
| N | H | H | F | H | H | H | OCH₃ |
| N | H | H | Cl | H | H | H | H |
| N | H | H | Cl | F | H | H | H |
| N | H | H | Cl | H | F | H | H |
| N | H | H | Cl | H | Cl | H | H |
| N | H | H | Cl | H | CH₃ | H | H |
| N | H | H | Cl | H | CF₃ | H | H |
| N | H | H | Cl | H | OCH₃ | H | H |
| N | H | H | Cl | H | H | F | H |
| N | H | H | Cl | H | H | H | F |
| N | H | H | Cl | H | H | H | Cl |
| N | H | H | Cl | H | H | H | CH₃ |
| N | H | H | Cl | H | H | H | CF₃ |
| N | H | H | Cl | H | H | H | OCH₃ |
| O | H | H | H | H | H | H | H |
| O | H | H | H | F | H | H | H |
| O | H | H | H | H | F | H | H |
| O | H | H | H | H | Cl | H | H |
| O | H | H | H | H | CH₃ | H | H |
| O | H | H | H | H | CF₃ | H | H |
| O | H | H | H | H | OCH₃ | H | H |
| O | H | H | H | H | H | F | H |
| O | H | H | H | H | H | H | F |
| O | H | H | H | H | H | H | Cl |
| O | H | H | H | H | H | H | CH₃ |
| O | H | H | H | H | H | H | CF₃ |
| O | H | H | H | H | H | H | OCH₃ |
| O | F | H | H | H | H | H | H |
| O | F | H | H | F | H | H | H |
| O | F | H | H | H | F | H | H |
| O | F | H | H | H | Cl | H | H |
| O | F | H | H | H | CH₃ | H | H |
| O | F | H | H | H | CF₃ | H | H |
| O | F | H | H | H | OCH₃ | H | H |
| O | F | H | H | H | H | F | H |
| O | F | H | H | H | H | H | F |
| O | F | H | H | H | H | H | Cl |
| O | F | H | H | H | H | H | CH₃ |
| O | F | H | H | H | H | H | CF₃ |
| O | F | H | H | H | H | H | OCH₃ |
| O | Cl | H | H | H | H | H | H |
| O | Cl | H | H | F | H | H | H |
| O | Cl | H | H | H | F | H | H |
| O | Cl | H | H | H | Cl | H | H |
| O | Cl | H | H | H | CH₃ | H | H |
| O | Cl | H | H | H | CF₃ | H | H |
| O | Cl | H | H | H | OCH₃ | H | H |
| O | Cl | H | H | H | H | F | H |
| O | Cl | H | H | H | H | H | F |
| O | Cl | H | H | H | H | H | Cl |
| O | Cl | H | H | H | H | H | CH₃ |
| O | Cl | H | H | H | H | H | CF₃ |
| O | Cl | H | H | H | H | H | OCH₃ |
| O | H | F | H | H | H | H | H |
| O | H | F | H | F | H | H | H |
| O | H | F | H | H | F | H | H |
| O | H | F | H | H | Cl | H | H |
| O | H | F | H | H | CH₃ | H | H |
| O | H | F | H | H | CF₃ | H | H |
| O | H | F | H | H | OCH₃ | H | H |
| O | H | F | H | H | H | F | H |
| O | H | F | H | H | H | H | F |
| O | H | F | H | H | H | H | Cl |
| O | H | F | H | H | H | H | CH₃ |
| O | H | F | H | H | H | H | CF₃ |
| O | H | F | H | H | H | H | OCH₃ |
| O | H | Cl | H | H | H | H | H |
| O | H | Cl | H | F | H | H | H |
| O | H | Cl | H | H | F | H | H |
| O | H | Cl | H | H | Cl | H | H |
| O | H | Cl | H | H | CH₃ | H | H |
| O | H | Cl | H | H | CF₃ | H | H |
| O | H | Cl | H | H | OCH₃ | H | H |
| O | H | Cl | H | H | H | F | H |
| O | H | Cl | H | H | H | H | F |
| O | H | Cl | H | H | H | H | Cl |
| O | H | Cl | H | H | H | H | CH₃ |
| O | H | Cl | H | H | H | H | CF₃ |
| O | H | Cl | H | H | H | H | OCH₃ |
| O | H | H | F | H | H | H | H |
| O | H | H | F | F | H | H | H |
| O | H | H | F | H | F | H | H |
| O | H | H | F | H | Cl | H | H |
| O | H | H | F | H | CH₃ | H | H |
| O | H | H | F | H | CF₃ | H | H |
| O | H | H | F | H | OCH₃ | H | H |
| O | H | H | F | H | H | F | H |
| O | H | H | F | H | H | H | F |
| O | H | H | F | H | H | H | Cl |
| O | H | H | F | H | H | H | CH₃ |
| O | H | H | F | H | H | H | CF₃ |
| O | H | H | F | H | H | H | OCH₃ |
| O | H | H | Cl | H | H | H | H |
| O | H | H | Cl | F | H | H | H |
| O | H | H | Cl | H | F | H | H |
| O | H | H | Cl | H | Cl | H | H |
| O | H | H | Cl | H | CH₃ | H | H |
| O | H | H | Cl | H | CF₃ | H | H |
| O | H | H | Cl | H | OCH₃ | H | H |
| O | H | H | Cl | H | H | F | H |
| O | H | H | Cl | H | H | H | F |
| O | H | H | Cl | H | H | H | Cl |
| O | H | H | Cl | H | H | H | CH₃ |
| O | H | H | Cl | H | H | H | CF₃ |
| O | H | H | Cl | H | H | H | OCH₃ |

Preferably, the achiral compound of formula (Ig)

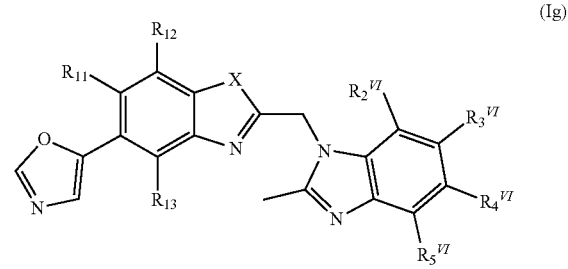

(Ig)

is selected from the group consisting of compounds of the formula (I), wherein $R_{11}$, $R_{12}$, $R_{13}$, $R_2^{VI}$, $R_3^{VI}$, $R_4^{VI}$ and $R_5^{VI}$ are as indicated in Table 7:

TABLE 7

| X | $R_{11}$ | $R_{12}$ | $R_{13}$ | $R_2^{VI}$ | $R_3^{VI}$ | $R_4^{VI}$ | $R_5^{VI}$ |
|---|---|---|---|---|---|---|---|
| N | H | H | H | H | H | H | H |
| N | H | H | H | F | H | H | H |
| N | H | H | H | H | F | H | H |
| N | H | H | H | H | Cl | H | H |
| N | H | H | H | H | $CH_3$ | H | H |
| N | H | H | H | H | $CF_3$ | H | H |
| N | H | H | H | H | $OCH_3$ | H | H |
| N | H | H | H | H | H | F | H |
| N | H | H | H | H | H | H | F |
| N | H | H | H | H | H | H | Cl |
| N | H | H | H | H | H | H | $CH_3$ |
| N | H | H | H | H | H | H | $CF_3$ |
| N | H | H | H | H | H | H | $OCH_3$ |
| N | F | H | H | H | H | H | H |
| N | F | H | H | F | H | H | H |
| N | F | H | H | H | F | H | H |
| N | F | H | H | H | Cl | H | H |
| N | F | H | H | H | $CH_3$ | H | H |
| N | F | H | H | H | $CF_3$ | H | H |
| N | F | H | H | H | $OCH_3$ | H | H |
| N | F | H | H | H | H | F | H |
| N | F | H | H | H | H | H | F |
| N | F | H | H | H | H | H | Cl |
| N | F | H | H | H | H | H | $CH_3$ |
| N | F | H | H | H | H | H | $CF_3$ |
| N | F | H | H | H | H | H | $OCH_3$ |
| N | Cl | H | H | H | H | H | H |
| N | Cl | H | H | F | H | H | H |
| N | Cl | H | H | H | F | H | H |
| N | Cl | H | H | H | Cl | H | H |
| N | Cl | H | H | H | $CH_3$ | H | H |
| N | Cl | H | H | H | $CF_3$ | H | H |
| N | Cl | H | H | H | $OCH_3$ | H | H |
| N | Cl | H | H | H | H | F | H |
| N | Cl | H | H | H | H | H | F |
| N | Cl | H | H | H | H | H | Cl |
| N | Cl | H | H | H | H | H | $CH_3$ |
| N | Cl | H | H | H | H | H | $CF_3$ |
| N | Cl | H | H | H | H | H | $OCH_3$ |
| N | H | F | H | H | H | H | H |
| N | H | F | H | F | H | H | H |
| N | H | F | H | H | F | H | H |
| N | H | F | H | H | Cl | H | H |
| N | H | F | H | H | $CH_3$ | H | H |
| N | H | F | H | H | $CF_3$ | H | H |
| N | H | F | H | H | $OCH_3$ | H | H |
| N | H | F | H | H | H | F | H |
| N | H | F | H | H | H | H | F |
| N | H | F | H | H | H | H | Cl |
| N | H | F | H | H | H | H | $CH_3$ |
| N | H | F | H | H | H | H | $CF_3$ |
| N | H | F | H | H | H | H | $OCH_3$ |
| N | H | Cl | H | H | H | H | H |
| N | H | Cl | H | F | H | H | H |
| N | H | Cl | H | H | F | H | H |
| N | H | Cl | H | H | Cl | H | H |
| N | H | Cl | H | H | $CH_3$ | H | H |
| N | H | Cl | H | H | $CF_3$ | H | H |
| N | H | Cl | H | H | $OCH_3$ | H | H |
| N | H | Cl | H | H | H | F | H |
| N | H | Cl | H | H | H | H | F |
| N | H | Cl | H | H | H | H | Cl |
| N | H | Cl | H | H | H | H | $CH_3$ |
| N | H | Cl | H | H | H | H | $CF_3$ |
| N | H | Cl | H | H | H | H | $OCH_3$ |
| N | H | H | F | H | H | H | H |
| N | H | H | F | F | H | H | H |
| N | H | H | F | H | F | H | H |
| N | H | H | F | H | Cl | H | H |
| N | H | H | F | H | $CH_3$ | H | H |
| N | H | H | F | H | $CF_3$ | H | H |
| N | H | H | F | H | $OCH_3$ | H | H |
| N | H | H | F | H | H | F | H |
| N | H | H | F | H | H | H | F |
| N | H | H | F | H | H | H | Cl |
| N | H | H | F | H | H | H | $CH_3$ |
| N | H | H | F | H | H | H | $CF_3$ |
| N | H | H | F | H | H | H | $OCH_3$ |
| N | H | H | Cl | H | H | H | H |
| N | H | H | Cl | F | H | H | H |
| N | H | H | Cl | H | F | H | H |
| N | H | H | Cl | H | Cl | H | H |
| N | H | H | Cl | H | $CH_3$ | H | H |
| N | H | H | Cl | H | $CF_3$ | H | H |
| N | H | H | Cl | H | $OCH_3$ | H | H |
| N | H | H | Cl | H | H | F | H |
| N | H | H | Cl | H | H | H | F |
| N | H | H | Cl | H | H | H | Cl |
| N | H | H | Cl | H | H | H | $CH_3$ |
| N | H | H | Cl | H | H | H | $CF_3$ |
| N | H | H | Cl | H | H | H | $OCH_3$ |
| O | H | H | H | H | H | H | H |
| O | H | H | H | F | H | H | H |
| O | H | H | H | H | F | H | H |
| O | H | H | H | H | Cl | H | H |
| O | H | H | H | H | $CH_3$ | H | H |
| O | H | H | H | H | $CF_3$ | H | H |
| O | H | H | H | H | $OCH_3$ | H | H |
| O | H | H | H | H | H | F | H |
| O | H | H | H | H | H | H | F |
| O | H | H | H | H | H | H | Cl |
| O | H | H | H | H | H | H | $CH_3$ |
| O | H | H | H | H | H | H | $CF_3$ |
| O | H | H | H | H | H | H | $OCH_3$ |
| O | F | H | H | H | H | H | H |
| O | F | H | H | F | H | H | H |
| O | F | H | H | H | F | H | H |
| O | F | H | H | H | Cl | H | H |
| O | F | H | H | H | $CH_3$ | H | H |
| O | F | H | H | H | $CF_3$ | H | H |
| O | F | H | H | H | $OCH_3$ | H | H |
| O | F | H | H | H | H | F | H |
| O | F | H | H | H | H | H | F |
| O | F | H | H | H | H | H | Cl |
| O | F | H | H | H | H | H | $CH_3$ |
| O | F | H | H | H | H | H | $CF_3$ |
| O | F | H | H | H | H | H | $OCH_3$ |
| O | Cl | H | H | H | H | H | H |
| O | Cl | H | H | F | H | H | H |
| O | Cl | H | H | H | F | H | H |
| O | Cl | H | H | H | Cl | H | H |
| O | Cl | H | H | H | $CH_3$ | H | H |
| O | Cl | H | H | H | $CF_3$ | H | H |
| O | Cl | H | H | H | $OCH_3$ | H | H |
| O | Cl | H | H | H | H | F | H |
| O | Cl | H | H | H | H | H | F |
| O | Cl | H | H | H | H | H | Cl |
| O | Cl | H | H | H | H | H | $CH_3$ |
| O | Cl | H | H | H | H | H | $CF_3$ |
| O | Cl | H | H | H | H | H | $OCH_3$ |
| O | H | F | H | H | H | H | H |
| O | H | F | H | F | H | H | H |
| O | H | F | H | H | F | H | H |
| O | H | F | H | H | Cl | H | H |
| O | H | F | H | H | $CH_3$ | H | H |
| O | H | F | H | H | $CF_3$ | H | H |
| O | H | F | H | H | $OCH_3$ | H | H |
| O | H | F | H | H | H | F | H |
| O | H | F | H | H | H | H | F |
| O | H | F | H | H | H | H | Cl |
| O | H | F | H | H | H | H | $CH_3$ |
| O | H | F | H | H | H | H | $CF_3$ |
| O | H | F | H | H | H | H | $OCH_3$ |
| O | H | Cl | H | H | H | H | H |
| O | H | Cl | H | F | H | H | H |
| O | H | Cl | H | H | F | H | H |
| O | H | Cl | H | H | Cl | H | H |
| O | H | Cl | H | H | $CH_3$ | H | H |
| O | H | Cl | H | H | $CF_3$ | H | H |
| O | H | Cl | H | H | $OCH_3$ | H | H |
| O | H | Cl | H | H | H | F | H |
| O | H | Cl | H | H | H | H | F |
| O | H | Cl | H | H | H | H | Cl |
| O | H | Cl | H | H | H | H | $CH_3$ |
| O | H | Cl | H | H | H | H | $CF_3$ |
| O | H | Cl | H | H | H | H | $OCH_3$ |

TABLE 7-continued

| X | $R_{11}$ | $R_{12}$ | $R_{13}$ | $R_2^{VI}$ | $R_3^{VI}$ | $R_4^{VI}$ | $R_5^{VI}$ |
|---|---|---|---|---|---|---|---|
| O | H | H | F | H | H | H | H |
| O | H | H | F | F | H | H | H |
| O | H | H | F | H | F | H | H |
| O | H | H | F | H | Cl | H | H |
| O | H | H | F | H | CH$_3$ | H | H |
| O | H | H | F | H | CF$_3$ | H | H |
| O | H | H | F | H | OCH$_3$ | H | H |
| O | H | H | F | H | H | F | H |
| O | H | H | F | H | H | H | F |
| O | H | H | F | H | H | H | Cl |
| O | H | H | F | H | H | H | CH$_3$ |
| O | H | H | F | H | H | H | CF$_3$ |
| O | H | H | F | H | H | H | OCH$_3$ |
| O | H | H | Cl | H | H | H | H |
| O | H | H | Cl | F | H | H | H |
| O | H | H | Cl | H | F | H | H |
| O | H | H | Cl | H | Cl | H | H |
| O | H | H | Cl | H | CH$_3$ | H | H |
| O | H | H | Cl | H | CF$_3$ | H | H |
| O | H | H | Cl | H | OCH$_3$ | H | H |
| O | H | H | Cl | H | H | F | H |
| O | H | H | Cl | H | H | H | F |
| O | H | H | Cl | H | H | H | Cl |
| O | H | H | Cl | H | H | H | CH$_3$ |
| O | H | H | Cl | H | H | H | CF$_3$ |
| O | H | H | Cl | H | H | H | OCH$_3$ |

Especially good results could be obtained by the following compounds according to the present invention:

TABLE 8

| Comp. No. | Chemical structure | Relative Pigmentation | Relative Growth |
|---|---|---|---|
| 1 | (R)-enantiomer, benzimidazole with oxazole substituent linked to chroman; enantiomer with the shorter retention time from the chiral HPLC resolution | 4.98 | 1.7 |
| 2 | (S)-enantiomer, benzimidazole with oxazole substituent linked to chroman; enantiomer with the longer retention time from the chiral HPLC resolution | 1.59 | 1.25 |
| 3 | benzimidazole with oxazole substituent linked to 2,3-dihydrobenzofuran (racemate) | 2.77 | 1.36 |
| 4 | benzimidazole with oxazole substituent linked to 7-fluoro-chroman (racemate) | 5.08 | 1.78 |
| 5 | benzimidazole with oxazole substituent linked to 6-chloro-chroman (racemate) | 1.04 | 1.52 |

TABLE 8-continued

| Comp. No. | Chemical structure | Relative Pigmentation | Relative Growth |
|---|---|---|---|
| 6 | 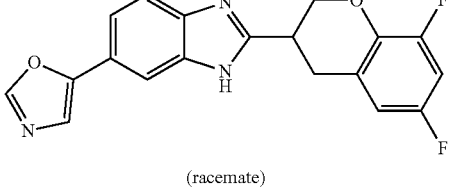<br>(racemate) | 2.30 | 1.42 |
| 7 | 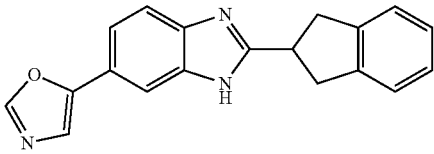 [SMILES: c1ccc2c(c1)CC(c1nc3ccc(-c4cnco4)cc3[nH]1)C2] | 2.36 | 1.34 |
| 8 | 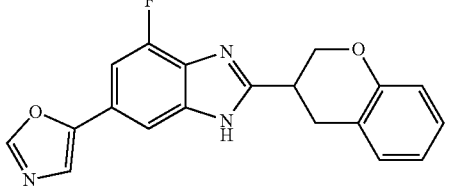<br>(racemate) | 2.75 | 1.49 |
| 9 | 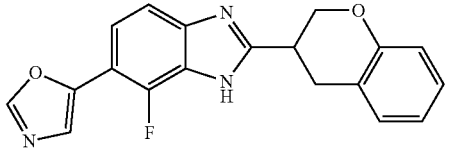 [SMILES: Fc1c(-c2cnco2)ccc2nc(C3COc4ccccc4C3)[nH]c12]<br>(racemate) | 4.27 | 1.13 |
| 10 | 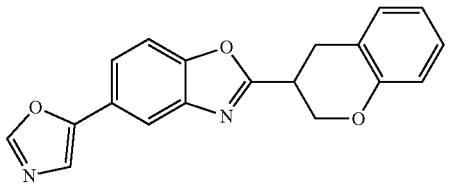 [SMILES: c1ccc2c(c1)CC(c1nc3cc(-c4cnco4)ccc3o1)CO2]<br>enantiomer with the longer retention time from the chiral HPLC resolution | 1.71 | 1.12 |
| 11 | 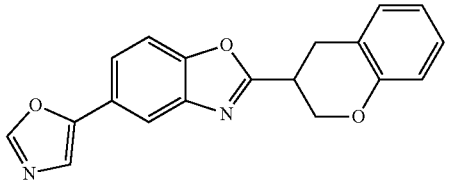 [SMILES: c1ccc2c(c1)CC(c1nc3cc(-c4cnco4)ccc3o1)CO2]<br>enantiomer with the shorter retention time from the chiral HPLC resolution | 6.24 | 1.42 |
| C* | — | 1 | 1 |

C* = Control experiment (absence of a compound according to the present invention)

The expression "enantiomer with the shorter retention time from the chiral HPLC resolution" means that the enantiomer comes first in the chiral HPLC when applying the conditions described in the corresponding Chiral Separation Methods. Within the context of the present invention the enantiomer with the shorter retention time is also called "first enantiomer" and the one with the longer retention time "second enantiomer".

As already mentioned, the compounds according to the present invention and the compositions according to the present invention stimulate the proliferation and/or differentiation of RPE cells. Thus, the compounds according to the present invention can be used in the treatment and/or prevention of RPE-related diseases, in particular of RPE diseases from the family of macular degeneration leading to loss of vision. Most preferably, the disease is a disease leading to atrophy, degeneration or death of the retinal pigment epithelium that might further result in retinal neovascularization and/or death of photoreceptors.

Compounds and compositions according to the present invention are particularly useful in the treatment and/or prevention of disease selected from the group of the family of macular degenerations consisting of early age-related macular degeneration (AMD), dry AMD and geographic atrophy (GA) as well as wet AMD by inducing the proliferation and/or differentiation of RPE cells. Thus, due to the compounds and compositions of the present invention, it is possible to reverse RPE cell damage caused by an illness by restoring or regenerating endogenous RPE cells, and not only to treat the loss of vision caused by RPE cell dysfunction and/or damage.

Compounds of formula (I) of the invention can be used, inter alia, to prevent the onset of dry age-related macular degeneration (dry AMD) and/or wet age-related macular degeneration (wet AMD), to prevent the progression of early AMD to advanced forms of AMD including wet AMD or geographic atrophy (GA), to slow and/or prevent progression of GA, to prevent or reduce the loss of vision from AMD, and to improve vision lost due to pre-existing early or advanced dry or wet AMD. It can also be used in combination with anti-VEGF therapies for the treatment of neovascular AMD patients or for the prevention of neovascular AMD.

Compounds and compositions according to the present invention are also useful in the treatment and/or prevention of disease selected from the group consisting of Best disease, autosomal recessive bestrophinopathy (ARB), gyrate atrophy, North Carolina macular dystrophy, central areolar choroidal dystrophy (CACD), Sorsby macular dystrophy, familial dominant drusen, cuticular or basal laminar drusen, retinopathy of prematurity, myopic degeneration, polypoidal choroidal vasculopathy (PCV), central serous retinopathy, angioid streaks, retinal detachment, retinal dialysis, Vogt-Koyanagi-Harada (VKH), acute posterior multifocal placoid pigment epitheliopathy (APMPPE), persistent placoid maculopathy (PPM) relentless placoid chorioretinopathy (RPC), serpiginous choroiditis, serpiginous-like choroiditis (multifocal serpiginoid choroiditis), multiple evanescence white dot syndrome (MEWDS) or Birdshot uveitis (vitiliginous chorioretinitis).

Compounds and compositions according to the present invention are particularly useful in the treatment and/or prevention of disease selected from the group consisting of a retinal disease leading to choroidal neovascularizatation or vascular leakage. Said retinal diseases are preferably selected from the group consisting of toxoplasmosis, toxocariasis, rubella, Behçets disease, choroidal hemangioma, trauma, choroidal rupture and idiopathic retinitis-vasculitis-aneurysms and neuroretinitis (IRVAN).

Compounds and compositions according to the present invention are particularly useful in the treatment and/or prevention of disease selected from the group consisting of a retinal disease that causes retinal inflammation and degeneration like sympathetic ophthalmia, post-operative inflammation or non-arteritic ischemic optic neuropathy as well as retinal degeneration associated with systemic disease such as diabetes mellitus, sickle cell disease or radiation retinopathy.

In a further embodiment, the present invention relates to a pharmaceutical composition for use in the treatment and/or prevention of a disease involving the retinal pigment epithelium, said pharmaceutical composition comprising a pharmaceutically acceptable carrier and/or adjuvant; and a compound of the formula (I)

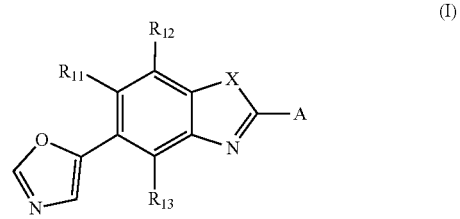

or a pharmaceutically acceptable salt, a racemic mixture, a corresponding tautomer, a corresponding enantiomer or, if applicable, a corresponding diastereomer thereof,
wherein:
X is either NH or O,
$R_{11}$, $R_{12}$ and $R_{13}$ are independently selected from the group consisting of hydrogen, fluoro, chloro, trifluoromethyl, methyl and difluoromethoxy,
A is selected from the group consisting of a residue of formula (II), (III), (IV), (V), (VI), (VII) or (VIII)

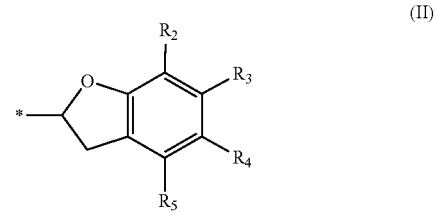

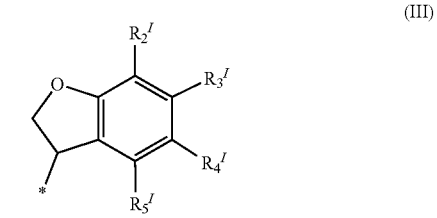

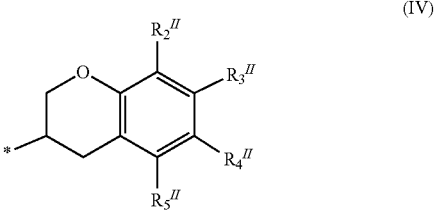

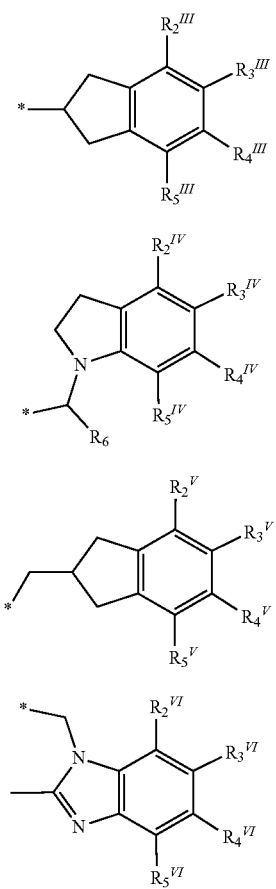

wherein,

"*" denotes the point of attachment to the remainder of the molecule, and $R_2, R_3, R_4, R_5, R_2^I, R_3^I, R_4^I, R_5^I, R_2^{II}, R_3^{II}, R_4^{II}, R_5^{II}, R_2^{III}, R_3^{III}, R_4^{III}, R_5^{III}, R_2^{IV}, R_3^{IV}, R_4^{IV}, R_5^{IV}, R_2^V, R_3^V, R_4^V, R_5^V, R_2^{VI}, R_3^{VI}, R_4^{VI}$ and $R_5^{VI}$ are independently selected from the group consisting of hydrogen, a linear or branched alkyl having 1 to 3 carbon atoms, fluoro, chloro, bromo, methoxy, ethoxy, propoxy, trifluoromethyl, 2,2,2-trifluoroethyl and difluoromethoxy and in the residue of formula (VI) $R_6$ is selected from the group consisting of hydrogen, a linear or branched alkyl having 1 to 3 carbon atoms, trifluoromethyl, and 2,2,2-trifluoroethyl as a therapeutically active substance.

The compound or the composition according to the present invention can be administered to a patient, either alone or in combination with one or more additional therapeutic agents. "Patient" as used herein, includes mammals such as humans, non-human primates, rats, mice, rabbits, hares, dogs, cats, horses, cows and pigs, preferably human.

The pharmaceutical composition according to the present invention may comprise one or more additional therapeutic agents.

In a preferred embodiment of the present invention, the pharmaceutical composition comprises a pharmaceutically acceptable carrier and/or adjuvant; and a compound of the formula (I) as defined above, preferably a compound of formula (Ia), (Ib), (Ic), (Id), (Ie), (If) or (Ig). Most preferably, it comprises a compound of formula (Ia), (Ib), (Ic), (Id), (Ie), (If) or (Ig) as disclosed in Table 1, Table 2, Table 3, Table 4, Table 5, Table 6 or Table 7 above. The compounds disclosed in Table 8 are particularly preferred.

Preferably, such a pharmaceutical composition provides controlled release properties. The term "controlled release pharmaceutical compositions" herein refers to any composition or dosage form, which comprises the compound of the present invention and which is formulated to provide a longer duration of pharmacological response after administration of the dosage form than is ordinarily experienced after administration of a corresponding immediate release composition comprising the same drug in the same amount. Controlled release may be extended up to several months depending on the matrix used. Preferably, the release of the compound according to the present invention takes place over a period of up to 12 months, most preferably over a period of up to 6 months, ideally up to 3 months. Such a controlled release formulation results in an increased patient comfort and in significant lower costs.

The matrix material used for a pharmaceutical composition according to the present may comprise hydrophobic release controlling agents. It is preferably selected from but not limited to polyvinyl acetate dispersion, ethyl cellulose, cellulose acetate, cellulose propionate (lower, medium or higher molecular weight), cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), waxes such as beeswax, carnauba wax, paraffin wax, microcrystalline wax, and ozokerite; fatty alcohols such as cetostearyl alcohol, stearyl alcohol, cetyl alcohol and myristyl alcohol, and fatty acid esters such as glyceryl monostearate; glycerol monooleate, acetylated monoglycerides, tristearin, tripalmitin, cetyl esters wax, glyceryl palmitostearate, glyceryl behenate, or hydrogenated vegetable oils.

The compound of the invention can be delivered to the eye through a variety of routes, including but not limited to topical application to the eye or by intraocular injection into, for example, the vitreous, subretinal (interphotoreceptor) or subconjunctival space; locally by insertion or injection into the tissue surrounding the eye; systemically through an oral route or by subcutaneous, intravenous or intramuscular injection; or via catheter or implant. Most preferably, the compound of the present invention is delivered by intraocular injection. Examples for topical ophthalmic compositions are eye drops, ointments, gels, solutions and suspensions.

The compound of the invention can be administered prior to the onset of the condition to prevent its occurrence, such as during eye surgery, immediately after the onset of the pathological condition, or during the occurrence of an acute or protracted condition.

Depending on the intended mode of administration, the compound according to the present invention may be incorporated in any pharmaceutically acceptable dosage form, such as for example, liquids, including solutions, suspensions and emulsions, tablets, suppositories, pills, capsules, powders or the like, preferably dosage forms suitable for single administration of precise dosages, or sustained release dosage forms for continuous controlled administration. Most preferred are liquids.

Liquid pharmaceutically administrable dosage forms can be for example a solution, a suspension or an emulsion, preferably a suspension comprising a compound of the present invention and optional pharmaceutical adjutants in a carrier, such as for example, water, saline, aqueous dextrose, glycerol, hyaluronic acid, ethanol, DMSO and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate and triethanolamine oleate.

The present invention also relates to a method of the treating and/or preventing RPE-related diseases, comprising administering a compound of formula (I), preferably (Ia), (Ib), (Ic), (Id), (Ie), (If) or (Ig) or a pharmaceutically acceptable salt, a racemic mixture, a corresponding enantiomer or, if applicable, a corresponding diastereomer thereof to a patient having the retinal disease so as to be delivered to an eye of the patient in an amount effective to treat the retinal disease. The compounds of formula (Ia), (Ib), (Ic), (Id), (Ie), (If) and (Ig) are defined above in detail.

Experimental Section
Cell Culture

Induced pluripotent stem cell-derived fetal RPE (iPSC-fRPE) cells acquired from the University of California, Santa Barbara, were generated from human fetal RPE cells that were isolated and reprogramed to iPSC, then differentiated and sorted for cellular markers to collect RPE progenitors. Vials were transported frozen on dry ice and stored in −80° C.

For the phenotypic screens, iPSC-fRPE cells were thawed and cultured in Matrigel-coated flasks with N1VA media containing 1×MEM solution supplemented with 2.2 g/L Sodium Bicarbonate, 0.25 mg/ml Taurine, 0.02 ug/ml Hydrocortisone, 0.013 ug/ml Triiodo Thyronine, 0.1 ug/ml Lipoic acid, 1% MEM Non-Essential Amino Acids, 1% Penicilin/Streptomycin, 2% Neurocult SM1 supplement and 1% N1 supplement. For the initial cultures, Thiazovivin was added to the media at 2 µM for the first 24 hr of incubation, after which the media was replaced with fresh N1VA media for additional three-day incubation at 37° C. with 5% CO2.

iPSC-fRPE cells were plated with N1VA media at a density of 10,000 cells per well in Matrigel-coated 96-well plates and cultured for 24 h prior to the treatment with test compounds at a final concentration of 5 µM in 0.1% DMSO. Internal controls for each test plate were (a) 0.1% DMSO as a negative control and (b) 0.1% DMSO+10 ng/ml human recombinant bFGF (STEMCELL) as a positive control.

To identify compounds that promote RPE pigmentation, cells were maintained for a period of 32 days and treated with medium containing the test or control compounds according to the media exchange regimen (FIG. 1). The degree of pigmentation was quantified by measuring the light absorbance at 510 nm with Cytation5 imaging reader (BIOTEK). Pigmentation values are finally reported relative to plate internal DMSO controls.

To assess proliferation of RPE cells, a replicate of compound-treated RPE cells were fixed at Day 5 and stained with Hoechst 33342 to determine live cell number with fluorescent microscopy. Cell numbers are reported relative to plate internal DMSO controls.

Preparation of the Compounds of the Invention

The compounds of formula (I) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-X1N" (published with Wiley-Interscience, ISSN: 1934-4783). Preferred methods include, but are not limited to, those described below.

The schemes are representative of methods useful in synthesizing the compounds of the present invention and the supporting examples. They are not to constrain the scope of the invention in anyway.

GENERAL METHODS—SYNTHESIS

Method 1

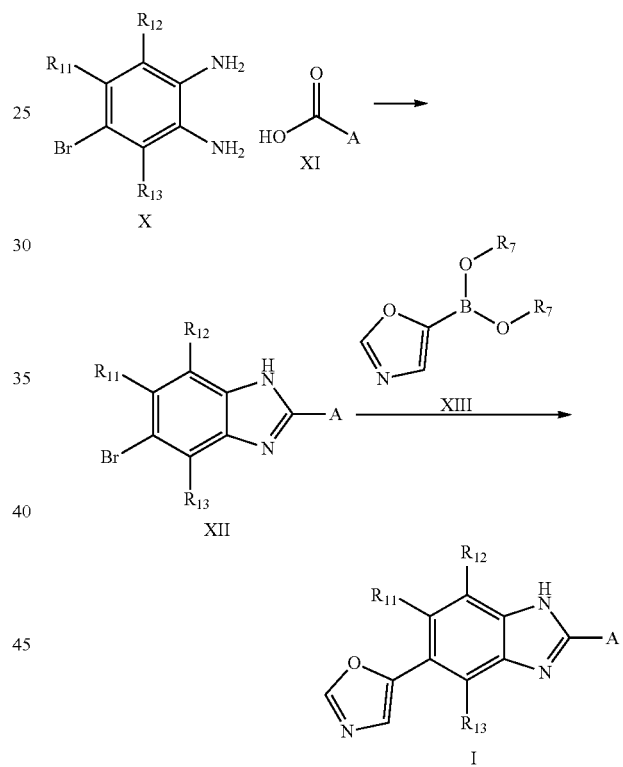

Scheme 1 where $R_{11}$, $R_{12}$, $R_{13}$ and A are as described in formula (I). $R_7$ are hydroxy groups or $R_7$ together with the boron atom form a 4,4,5,5-tetramethyl-1,3,2-dioxaborolane group.

Compounds of general formula (I) (Scheme 1) may be prepared from compounds of general formulae (XII) and (XIII) in the presence of a palladium catalyst such as tetrakis(triphenylphosphine)palladium(0) and a base such as potassium carbonate or other Suzuki-Miyaura coupling reaction conditions known to chemists skilled in the art of organic synthesis. Compounds of general formula (XII) may be prepared by reacting compounds of general formula (X) with a carboxylic acid of general formula (XI) using procedures known to chemists skilled in the art. The crude intermediate can be finally dehydrated for example using conditions such as heating in solvent as acetic acid.

Method 2

Scheme 2

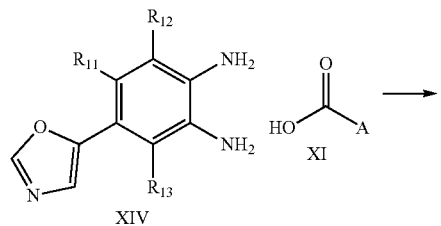

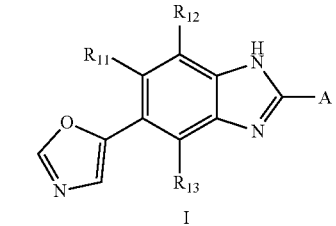

where $R_{11}$, $R_{12}$, $R_{13}$ and A are as described in formula (I).

Compounds of general formula (I) (Scheme 2) may be prepared by reacting compounds of general formula (XIV) with a carboxylic acid of general formula (XI) using procedures known to chemists skilled in the art. The crude intermediate can be finally dehydrated for example using conditions such as heating in solvent as acetic acid.

Method 3

Scheme 3

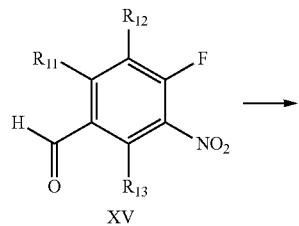

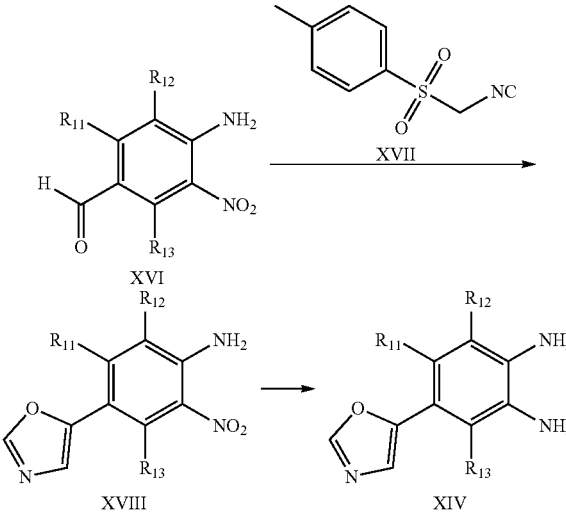

where $R_{11}$, $R_{12}$, $R_{13}$ are as described in formula (I).

Compounds of general formula (XIV) (Scheme 3) may be prepared by reduction of the nitro group in compounds of general formula (XVIII) using procedures known to chemists skilled in the art. Compounds of general formula (XVIII) may be prepared from aldehydes of general formula (XVI) by reaction in the presence of a reagent such as 1-((isocyanomethyl)sulfonyl)-4-methylbenzene (XVII) in the presence of a base such as potassium carbonate. Compounds of general formula (XVI) may be prepared by bubbling ammonia in a solution of compounds of general formula (XV) in a solvent such as dichloromethane at room temperature.

Method 4

Scheme 4

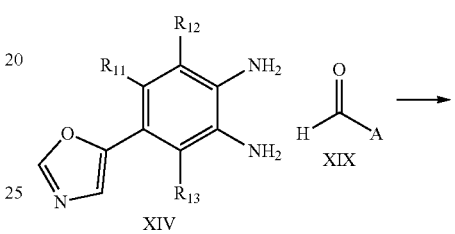

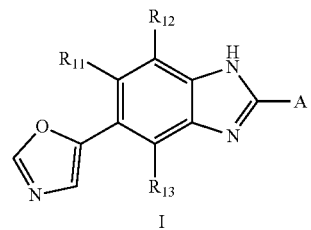

where $R_{11}$, $R_{12}$, $R_{13}$ and A are as described in formula (I).

Compounds of general formula (I) (Scheme 2) may be prepared by reacting compounds of general formula (XIV) with an aldehyde of general formula (XIX) in a solvent such as 1,4-dioxane and in the presence of an acid such as para-toluenesulfonic acid at high temperature.

Method 5

Scheme 5

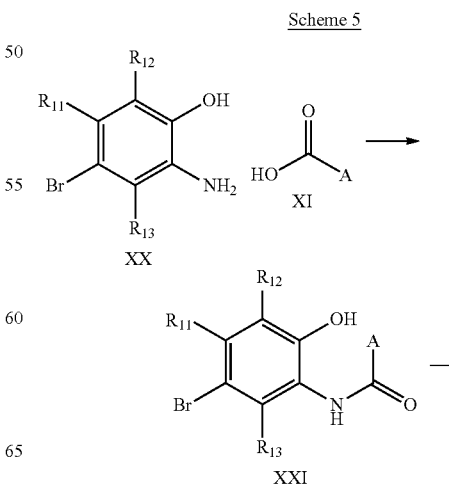

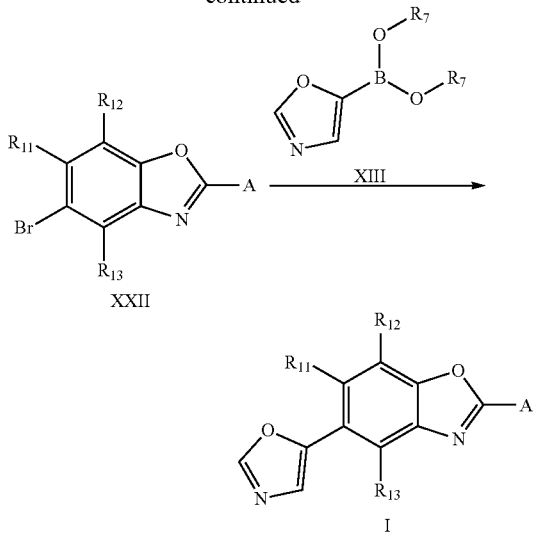

where $R_{11}$, $R_{12}$, $R_{13}$ and A are as described in formula (I). $R_7$ are hydroxy groups or $R_7$ together with the boron atom form a 4,4,5,5-tetramethyl-1,3,2-dioxaborolane group.

Compounds of general formula (I) (Scheme 1) may be prepared from compounds of general formulae (XXII) and (XIII) in the presence of a palladium catalyst such as tetrakis(triphenylphosphine)palladium(0) and a base such as potassium carbonate or other Suzuki-Miyaura coupling reaction conditions known to chemists skilled in the art of organic synthesis. Compounds of general formula (XXII) may be prepared by treating compounds of general formula (XXI) in the presence of a dehydrating agent such as phosphoryl chloride. Compounds of general formula (XXI) may be prepared by transforming compounds of general formula (XI) to the corresponding acyl chloride using reagents such as thionyl chloride and reacting them with compounds of general formula (XX).

Analytic Methods $^1$H NMR spectra were recorded in DMSO-$d_6$/CD$_3$OD/CDCl$_3$ solution in 5 mm o.d. tubes [Wilmad NMR tubes (Sigma-Aldrich), 5 mm Thin Wall, 7" Length] at 300.0 K and were collected on Bruker Avance NMRS-400 at 400 MHz for $^1$H. The chemical shifts (δ) are relative to CDCl$_3$ (CDCl$_3$=7.26 ppm), DMSO-$d_6$ (DMSO-$d_6$=2.5 ppm), CD$_3$OD (CD$_3$OD=3.3 ppm) and expressed in ppm. The chemical shifts in CDCl$_3$, DMSO-$d_6$ and CD$_3$OD are relative to tetramethylsilane (TMS, =0.00 ppm) and expressed in ppm.

Analytical HPLC

Analytical HPLC Method A:

Zorbax SB-C18 column (1.8 μm 4.6*15 mm, Rapid Resolution cartridge PN 821975-932) operated with a flow rate of 3 ml/min in an Agilent 1100 Series LC/MSD system with DAD\ELSD and Agilent LC\MSD VL (G1956A), SL (G1956B) mass-spectrometer using mobile phase A: acetonitrile, 0.1% formic acid; mobile phase B: water (0.1% formic acid); with the following gradient: 0 min-100% B; 0.01 min-100% B; 1.5 min-0% B; 1.8 min-0% B; 1.81 min-100% B.

Analytical HPLC Method B:

UPLC column YMC Triart C18 (33×2.1 mm, 3 μm) column operated at room temperature with a flow rate of 1.0 mL/min. Samples were eluted with mobile phase: 98% [10 mM ammonium acetate in water] and 2% [acetonitrile] held for 0.75 min then to 90% [10 mM ammonium acetate in water] and 10% [acetonitrile] in 1.0 min, further to 2% [10 mM ammonium acetate in water] and 98% [acetonitrile] in 2.0 min.

Chiral Analytical HPLC

Chiral Analytical HPLC Method A: chiral chromatography using Chiralpak IA (25*4.6, 5 μm) column; Hexane-IPA-MeOH, 90-5-5 as mobile phase; Flow 0.6 mL/min.

Preparative HPLC

Preparative HPLC Method A: Agilent 1260 Infinity systems equipped with DAD and mass-detector; Waters Sunfire C18 OBD Prep Column, 100 A, 5 μm, 19 mm*100 mm with SunFire C18 Prep Guard Cartridge, 100 A, 10 μm, 19 mm*10 mm; 30-85% 0-5 min H$_2$O-methanol, flow rate 30 mL/min).

Methods for Chiral Separation

Chiral Separation Method A: chiral chromatography using Chiralpak IA-II (250*20, 5 mkm) column; Hexane-IPA-MeOH, 80-10-10 as mobile phase; Flow 12 mL/min.

Chiral Separation Method B: SFC chiral chromatography (Reflect C-Amylose A (250×30 mm) 5p column, CO$_2$-(0.1% Ammonia in MeOH), 35%-65% as a mobile phase, P=110 bar, Flow 35 g/min, T=35° C.

General Synthetic Procedures

Synthetic Procedure A:

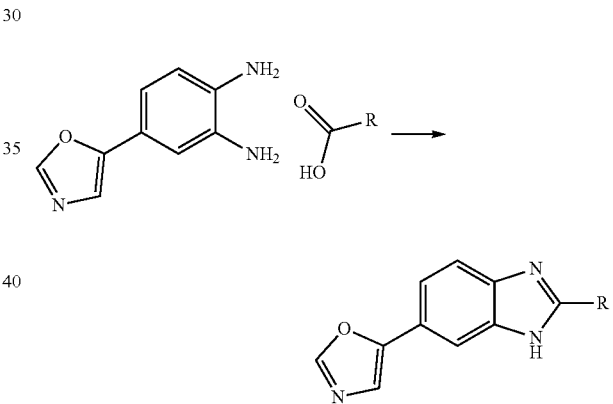

To a solution of carboxylic acid (1.22 mmol) in DMF (5 mL), ethylbis(propan-2-yl)amine (1.44 mmol, 1.18 equiv) and HATU (1.34 mmol) were added. The resulting mixture was stirred for 20 min at room temperature followed by the addition of 4-(1,3-oxazol-5-yl)benzene-1,2-diamine (1.34 mmol). The reaction mixture was stirred at room temperature overnight. Then, the suspension was concentrated under reduced pressure. The residue was diluted with ethyl acetate (50 ml), washed with aq. NaHCO$_3$ (2×20 ml) and brine (2×10 ml). The organic layer was dried over anhydrous sodium sulfate, filtered and concentrated under reduced pressure. The crude product was dissolved in acetic acid (5 ml) and the mixture was stirred at 60° C. overnight. The mixture was concentrated under reduced pressure, diluted with ethyl acetate (50 ml), basified with aq. NaHCO$_3$, washed with brine (10 ml), dried over anhydrous sodium sulfate, and concentrated under reduced pressure. The residue was purified by prep-HPLC using SunFireC18 100*19 mm 5 μm as column, (20-50% 0-5 min water-MeCN as eluent) and flow 30 ml/min.

Synthetic Procedure B:

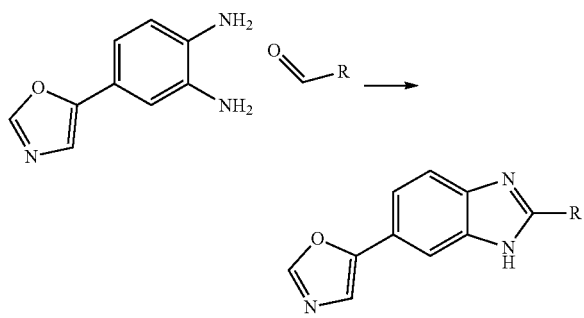

Aldehyde (1.43 mmol) and 4-(1,3-oxazol-5-yl)benzene-1,2-diamine (1.43 mmol) were mixed in 1,4-dioxane (5 ml). The resulting mixture was stirred for 5 min followed by the addition of 4-methylbenzene-1-sulfonic acid (0.29 mmol). The reaction mixture was stirred at 100° C. overnight. Then, the mixture was allowed to cool to room temperature, evaporated to dryness, and purified by Flash Chromatography.

Synthesis of Intermediates

Preparation of 4-amino-3-nitrobenzaldehyde

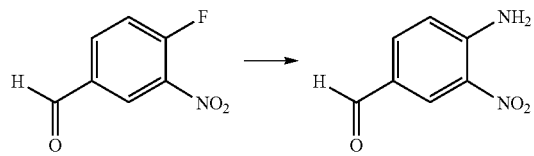 [SMILES: O=Cc1ccc(F)c([N+](=O)[O-])c1 ; Nc1ccc(C=O)cc1[N+](=O)[O-]]

To a stirred solution 4-fluoro-3-nitrobenzaldehyde (50.0 g, 295.67 mmol) in dichloromethane (1200 mL), ammonia was bubled for 30 min at 0° C. The mixture was stirred for additional 3 hours at room temperature and concentrated to obtain 4-amino-3-nitrobenzaldehyde (45.1 g, 271.47 mmol, 91.8% yield).

Preparation of 2-nitro-4-(1,3-oxazol-5-yl)aniline

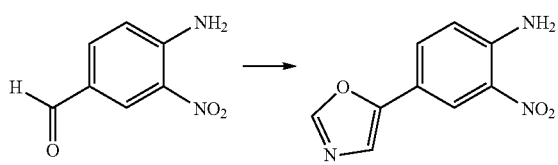 [SMILES: Nc1ccc(C=O)cc1[N+](=O)[O-] ; Nc1ccc(-c2cnco2)cc1[N+](=O)[O-]]

A solution of 4-amino-3-nitrobenzaldehyde (45.1 g, 271.47 mmol) in methanol (800 ml) was treated with 1-isocyanomethanesulfonyl-4-methylbenzene (79.5 g, 407.2 mmol) and potassium carbonate (39.39 g, 285.04 mmol). The reaction mixture was heated under reflux for 90 min. Then, the cooled solution was concentrated and treated with water (750 ml). The mixture was extracted with ethyl acetate (4*250 ml). The combined organic layer was washed with brine, water, dried over anhydrous sodium sulfate and concentrated. The crude product was purified by Flash Chromatography to obtain 2-nitro-4-(1,3-oxazol-5-yl)aniline (10.1 g, 49.23 mmol, 18.1% yield).

Preparation of 4-(1,3-oxazol-5-yl)benzene-1,2-diamine

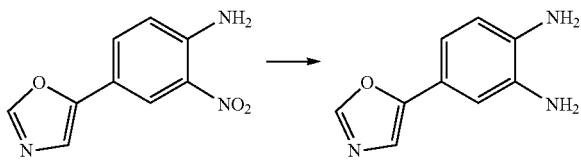 [SMILES: Nc1ccc(-c2cnco2)cc1[N+](=O)[O-] ; Nc1ccc(-c2cnco2)cc1N]

Pd(OH)$_2$ (410.75 mg, 2.92 mmol) (20% w/w) was added to a solution of 2-nitro-5-(1,3-oxazol-5-yl)aniline (3.0 g, 14.62 mmol) in THF (50 mL). The resulting mixture was stirred under hydrogen atmosphere at room temperature and atmospheric pressure overnight. The catalyst was removed through filtration, and the solvent was evaporated to afford 4-(1,3-oxazol-5-yl)benzene-1,2-diamine (2.1 g, 11.99 mmol, 82% yield).

Preparation of 5-(4,4,5,5-tetramethyl-1,3,2-dioxaborolan-2-yl)-2-[tris(propan-2-yl)silyl]-1,3-oxazole

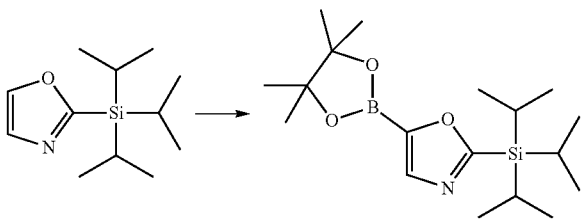 [SMILES: CC(C)[Si](c1ncco1)(C(C)C)C(C)C ; CC(C)[Si](c1ncc(B2OC(C)(C)C(C)(C)O2)o1)(C(C)C)C(C)C]

To the stirred solution of 2-[tris(propan-2-yl)silyl]-1,3-oxazole (2.07 g, 9.18 mmol) in 60 ml of dry THF, a 2.5 molar solution of n-butyllithium (11.0 mmol, 4.4 mL, 1.2 eq.) was added dropwise under argon at −78° C. The resulting mixture was stirred for 1 h at −78° C. followed by the dropwise addition of the solution of tris(propan-2-yl) borate (3.45 g, 18.37 mmol, 4.21 ml, 2.0 equiv) in 10 ml of THF at this temperature. The reaction mixture was stirred for 2 h at −78° C., then overnight at room temperature. Then, 2,3-dimethylbutane-2,3-diol (1.09 g, 9.18 mmol) and acetic acid (827.29 mg, 13.78 mmol, 800.0 µl, 1.5 equiv) were added. The obtained mixture was stirred at room temperature for 2 h. After that, the suspension was evaporated and the residue was diluted with water. The product was extracted with ethyl acetate, washed with brine, dried over sodium sulfate, and evaporated to obtain 5-(4,4,5,5-tetramethyl-1,3,2-dioxaborolan-2-yl)-2-[tris(propan-2-yl)silyl]-1,3-oxazole (3.0 g, 85.0% purity, 7.26 mmol, 79% yield).

Preparation of
N-(5-bromo-2-hydroxyphenyl)chromane-3-carboxamide

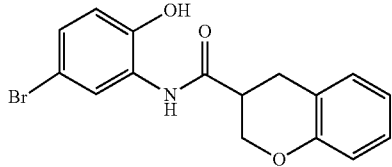 [SMILES: O=C(Nc1cc(Br)ccc1O)C1COc2ccccc2C1]

Chromane-3-carboxylic acid (2 g, 11.23 mmol) was dissolved in SOCl$_2$ (2 mL, 28.09 mmol) and stirred at room temperature for 24 h under nitrogen atmosphere. After that, the reaction mixture was concentrated in vacuum and diluted with dichloromethane (10 mL) under nitrogen atmosphere and the evaporation process was repeated twice. To a round bottomed flask was added 2-amino-4-bromophenol (2.3 g, 12.36 mmol) in dichloromethane (6 mL) along with pyridine (1 mL, 12.36 mmol). The mixture was stirred at room temperature for 15 min. In a second round bottomed flask containing the above mentioned freshly prepared chromane-3-carbonyl chloride (2) was added at room temperature, dichloromethane (4 mL), followed by the above mixture containing 2-amino-4-bromophenol (1) in dichloromethane. The combined reaction mixture was stirred 18 h at room temperature. The crude reaction mixture was extracted with dichloromethane, washed with water. The combined organic part was dried over sodium sulphate, filtered and evaporated in vacuum. The crude product was purified by amine silica gel column chromatography to afford AT-(5-bromo-2-hydroxyphenyl)chromane-3-carboxamide (3) (1.3 g, 33%).

Preparation of
5-bromo-2-(chroman-3-yl)benzo[d]oxazole

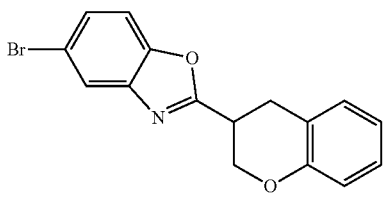 [SMILES: Brc1ccc2oc(C3COc4ccccc4C3)nc2c1]

To a stirred solution of N-(5-bromo-2-hydroxyphenyl)chromane-3-carboxamide (2.5 g, 7.18 mmol) in 1,4-dioxane (2 mL) was added POCl$_3$ (8 mL, 86.2 mmol) and the reaction mixture was sealed and refluxed at 110° C. for 2 h. After that, the reaction mixture was concentrated and purified by Flash Chromatography to afford 5-bromo-2-(chroman-3-yl)benzo[d]oxazole (800 mg, 33%).

Compound (1): "First" (R)-5-(2-(chroman-3-yl)-1H-benzo[d]imidazol-6-yl)oxazole

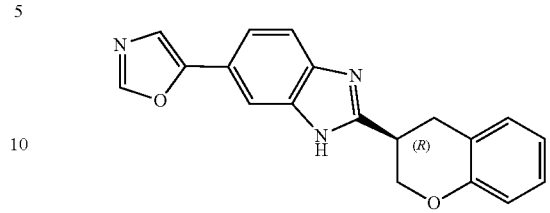

To a solution of the 3,4-dihydro-2H-1-benzopyran-3-carboxylic acid (5.0 g, 28.07 mmol) in DMF (200 mL), DIPEA (4.28 g, 33.13 mmol, 5.77 ml, 1.18 equiv) and HATU (11.74 g, 30.88 mmol) were added. The resulting mixture was stirred for 20 min at room temperature followed by the addition of 4-(1,3-oxazol-5-yl)benzene-1,2-diamine (5.41 g, 30.88 mmol). The reaction mixture was stirred at room temperature overnight. Then, the mixture was concentrated under reduced pressure, diluted with ethyl acetate (250 mL), washed with aq. NaHCO$_3$ (2×80 mL) and brine (2×50 mL), dried over anhydrous sodium sulfate, filtered and concentrated under reduced pressure. Without additional purification, the obtained crude product was dissolved in acetic acid (100 mL) and the mixture was stirred at 60° C. overnight. The resulting solution was evaporated in vacuo, diluted with ethyl acetate (250 mL), basified with aq. NaHCO$_3$, washed with brine (100 mL), dried over anhydrous sodium sulfate and concentrated under reduced pressure. The residue was purified using Preparative HPLC method A to yield 5-(2-(chroman-3-yl)-1H-benzo[d]imidazol-6-yl)oxazole.

Chiral separation of 5-(2-(chroman-3-yl)-1H-benzo[d]imidazol-6-yl)oxazole using Chiral Separation Method A yields Compound (1) (603.3 mg) characterized by retention time=19.7 min.

$[\alpha]_D^{25}$=−12.00 (c=0.25, MeOH).

[M+H$^+$] m/z: 318.2

$^1$H NMR (DMSO-d$_6$, 400 MHz): δ (ppm) 3.23 (m, 2H), 3.59 (m, 1H), 4.27 (t, 1H), 4.59 (d, 1H), 6.80 (d, 1H), 6.88 (t, 1H), 7.10 (t, 1H), 7.17 (d, 1H), 7.56 (d, 1H), 7.62 (m, 2H), 7.86 (s, 1H), 8.41 (s, 1H), 12.57 (s, 1H).

The structure was confirmed by X-ray.

Compound (2): "Second" (S)-5-(2-(chroman-3-yl)-1H-benzo[d]imidazol-6-yl)oxazole

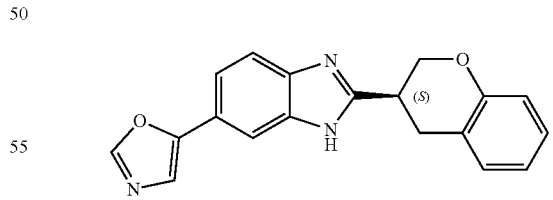

To a solution of the 3,4-dihydro-2H-1-benzopyran-3-carboxylic acid (5.0 g, 28.07 mmol) in DMF (200 mL), DIPEA (4.28 g, 33.13 mmol, 5.77 ml, 1.18 equiv) and HATU (11.74 g, 30.88 mmol) were added. The resulting mixture was stirred for 20 min at room temperature followed by the addition of 4-(1,3-oxazol-5-yl)benzene-1,2-diamine (5.41 g, 30.88 mmol). The reaction mixture was stirred at room temperature overnight. Then, the mixture was concentrated under reduced pressure, diluted with ethyl acetate (250 mL), washed with aq. NaHCO₃ (2×80 mL) and brine (2×50 mL), dried over anhydrous sodium sulfate, filtered and concentrated under reduced pressure. Without additional purification, the obtained crude product was dissolved in acetic acid (100 mL) and the mixture was stirred at 60° C. overnight. The resulting solution was evaporated in vacuo, diluted with ethyl acetate (250 mL), basified with aq. NaHCO₃, washed with brine (100 mL), dried over anhydrous sodium sulfate and concentrated under reduced pressure. The residue was purified using Preparative HPLC method A to yield 5-(2-(chroman-3-yl)-1H-benzo[d]imidazol-6-yl)oxazole.

Chiral separation of 5-(2-(chroman-3-yl)-1H-benzo[d]imidazol-6-yl)oxazole using Chiral Separation Method A yields Compound (2) (607.5 mg) characterized by retention time=27.4 min.

$[\alpha]_D^{25}$=+13.56 (c=0.25, MeOH).

[M+H⁺] m/z: 318.2

¹H NMR (DMSO-d₆, 400 MHz): δ (ppm) 3.25 (m, 2H), 3.59 (m, 1H), 4.27 (t, 1H), 4.59 (m, 1H), 6.80 (d, 1H), 6.88 (t, 1H), 7.10 (t, 1H), 7.17 (d, 1H), 7.61 (m, 3H), 7.86 (d, 1H), 8.41 (s, 1H), 12.63 (s, 1H).

Compound (3): 2-(2,3-dihydro-1-benzofuran-2-yl)-6-(1,3-oxazol-5-yl)-1H-1,3-benzodiazole

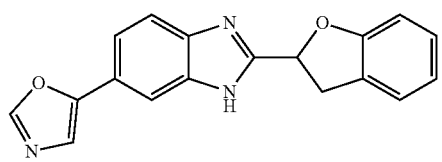 [SMILES: c1ccc2c(c1)CC(c1nc3ccc(-c4cnco4)cc3[nH]1)O2]

2,3-dihydro-1-benzofuran-2-carboxylic acid (0.2 g) was used in combination with Synthetic Procedure A to afford 2-(2,3-dihydro-1-benzofuran-2-yl)-6-(1,3-oxazol-5-yl)-1H-1,3-benzodiazole (63 mg, 14.0% yield).

Analytical HPLC Method A. [M+H⁺] m/z: 304.2; Rt=2.35 min.

Compound (4): 2-(7-fluoro-3,4-dihydro-2H-1-benzopyran-3-yl)-6-(1,3-oxazol-5-yl)-1H-1,3-benzodiazole

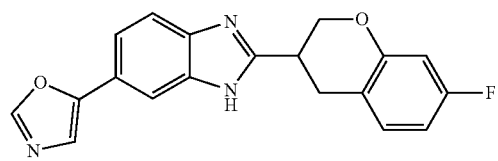 [SMILES: Fc1ccc2c(c1)OCC(c1nc3ccc(-c4cnco4)cc3[nH]1)C2]

7-fluoro-3,4-dihydro-2H-1-benzopyran-3-carboxylic acid (0.2 g) was used in combination with Synthetic Procedure A to afford 2-(7-fluoro-3,4-dihydro-2H-1-benzopyran-3-yl)-6-(1,3-oxazol-5-yl)-1H-1,3-benzodiazole (68 mg, 15.1% yield).

Analytical HPLC Method A. [M+H⁺] m/z: 336.2; Rt=2.35 min.

Compound (5): 2-(6-chloro-3,4-dihydro-2H-1-benzopyran-3-yl)-6-(1,3-oxazol-5-yl)-1H-1,3-benzodiazole

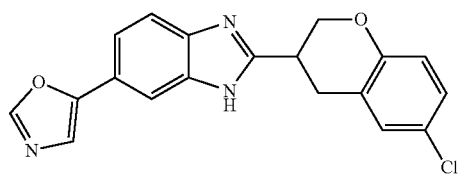 [SMILES: Clc1ccc2c(c1)CC(c1nc3ccc(-c4cnco4)cc3[nH]1)CO2]

6-fluoro-3,4-dihydro-2H-1-benzopyran-3-carbonyl chloride (0.17 g) was used in combination with Synthetic Procedure A to afford 2-(6-chloro-3,4-dihydro-2H-1-benzopyran-3-yl)-6-(1,3-oxazol-5-yl)-1H-1,3-benzodiazole (70 mg, 15.8% yield).

Analytical HPLC Method A. [M+H⁺] m/z: 352.0; Rt=2.54.

Compound (6): 2-(6,8-difluoro-3,4-dihydro-2H-1-benzopyran-3-yl)-6-(1,3-oxazol-5-yl)-1H-1,3-benzodiazole

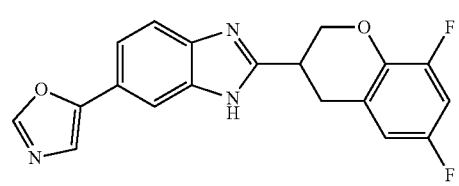 [SMILES: Fc1cc(F)c2c(c1)CC(c1nc3ccc(-c4cnco4)cc3[nH]1)CO2]

6,8-difluoro-3,4-dihydro-2H-1-benzopyran-3-carboxylic acid (0.2 g) was used in combination with Synthetic Procedure A to afford 2-(6,8-difluoro-3,4-dihydro-2H-1-benzopyran-3-yl)-6-(1,3-oxazol-5-yl)-1H-1,3-benzodiazole (39 mg, 8.6% yield).

Analytical HPLC Method A. [M+H⁺]m/z: 354.2; Rt=2.47 min.

Compound (7): 2-(2,3-dihydro-1H-inden-2-yl)-6-(1,3-oxazol-5-yl)-1H-1,3-benzodiazole

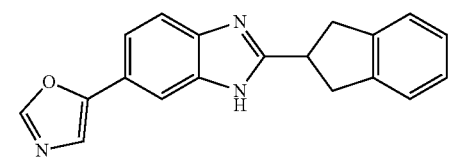 [SMILES: c1ccc2c(c1)CC(c1nc3ccc(-c4cnco4)cc3[nH]1)C2]

2,3-dihydro-1H-indene-2-carbaldehyde (0.098 g) was used in combination with Synthetic Procedure B to afford 2-(2,3-dihydro-1H-inden-2-yl)-6-(1,3-oxazol-5-yl)-1H-1,3-benzodiazole (30 mg, 10% yield).

Analytical HPLC Method A. [M+H⁺]m/z: 302.2; Rt=1.94 min.

Compound (8): 2-(3,4-dihydro-2H-1-benzopyran-3-yl)-7-fluoro-5-(1,3-oxazol-5-yl)-1H-1,3-benzodiazole

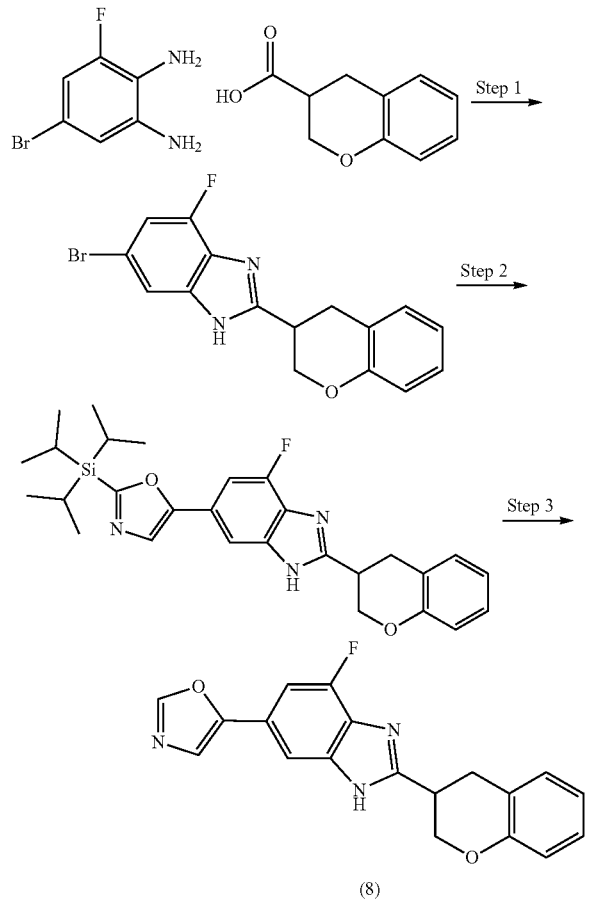

(8)

Step 1: 6-bromo-2-(3,4-dihydro-2H-1-benzopyran-3-yl)-4-fluoro-1H-1,3-benzodiazole To a solution of the 3,4-dihydro-2H-1-benzopyran-3-carboxylic acid (3.95 g, 22.17 mmol) in DMF (100 mL), ethylbis(propan-2-yl)amine (3.38 g, 26.16 mmol, 4.56 ml, 1.18 equiv) and HATU (9.27 g, 24.39 mmol) were added. The resulting mixture was stirred for 20 min followed by the addition of 5-bromo-3-fluorobenzene-1,2-diamine (5.0 g, 24.39 mmol). The reaction mixture was stirred at room temperature overnight. The resulting was concentrated under reduced pressure, diluted with ethyl acetate (250 mL), washed with aq. NaHCO$_3$ (2*75 mL) and brine (2*50 mL), dried over anhydrous sodium sulfate, filtered off and concentrated under reduced pressure. Without further purification, the crude product was dissolved in acetic acid (100 mL) and the mixture was stirred at 60° C. overnight. The mixture was concentrated under reduced pressure, diluted with ethyl acetate (250 mL), basified with aq. NaHCO$_3$, washed with brine (100 mL), dried over anhydrous sodium sulfate and concentrated under reduced pressure. The residue was purified by Flash Chromatography to afford 6-bromo-2-(3,4-dihydro-2H-1-benzopyran-3-yl)-4-fluoro-1H-1,3-benzodiazole (4.2 g, 12.1 mmol, 54.6% yield).

Step 2: 2-(3,4-dihydro-2H-1-benzopyran-3-yl)-7-fluoro-5-2-[tris(propan-2-yl)silyl]-1,3-oxazol-5-yl-1H-1,3-benzodiazole To the stirred solution of 5-bromo-2-(3,4-dihydro-2H-1-benzopyran-3-yl)-7-fluoro-1H-1,3-benzodiazole (2.72 g, 7.83 mmol) in 40 mL of dry dymethoxyethane and 13.5 mL of water were added under argon 5-(4,4,5,5-tetramethyl-1,3,2-dioxaborolan-2-yl)-2-[tris(propan-2-yl)silyl]-1,3-oxazole (5.5 g, 15.65 mmol), tetrakis(triphenylphosphine)palladium(0) (907.54 mg, 782.63 µmol) and potassium carbonate (3.24 g, 23.48 mmol). The reaction mixture was stirred for 20 min and room temperature, and then overnight at 80° C., The mixture was evaporated to dryness and purified by Flash Chromatography to obtain 2-(3,4-dihydro-2H-1-benzopyran-3-yl)-7-fluoro-5-2-[tris(propan-2-yl)silyl]-1,3-oxazol-5-yl-1H-1,3-benzodiazole (2.9 g, 5.9 mmol, 75.4% yield).

Step 3: 2-(3,4-dihydro-2H-1-benzopyran-3-yl)-4-fluoro-6-(1,3-oxazol-5-yl)-1H-1,3-benzodiazole To the stirred solution of 2-(3,4-dihydro-2H-1-benzopyran-3-yl)-7-fluoro-5-2-[tris(propan-2-yl)silyl]-1,3-oxazol-5-yl-1H-1,3-benzodiazole (2.9 g, 5.9 mmol) in 1.5 mL of THF, the solution of tetrabutyl ammonium fluoride (7.71 g, 29.49 mmol, 8.54 ml, 5.0 equiv) in THF was added. The reaction mixture was stirred overnight at room temperature, evaporated, diluted with water. extracted with ethyl acetate, washed with water, dried over sodium sulfate, evaporated and purified by column chromatography (SiO2, CHCl3-MeCN as a mobile phase) to obtain 2-(3,4-dihydro-2H-1-benzopyran-3-yl)-4-fluoro-6-(1,3-oxazol-5-yl)-1H-1,3-benzodiazole (1.3 g, 3.88 mmol, 65.7% yield).

Analytical HPLC Method A. [M+H$^+$] m/z: 336.2; Rt=2.76 min.

Compound (9): 2-(3,4-dihydro-2H-1-benzopyran-3-yl)-4-fluoro-5-(1,3-oxazol-5-yl)-1H-1,3-benzodiazole

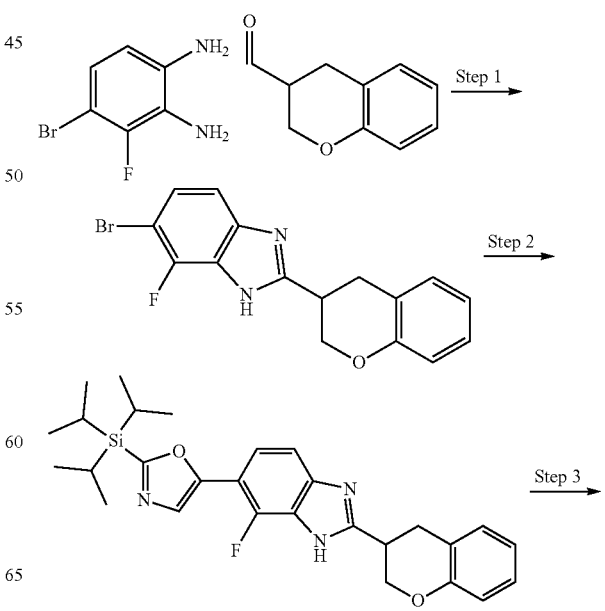

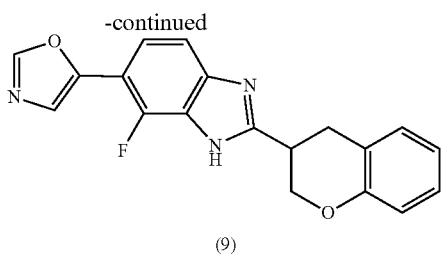

(9)

4-bromo-3-fluorobenzene-1,2-diamine (1 g) was used in the same 3 step synthetic procedure and molar ratio as Compound 12 to afford 6-chloro-2-(3,4-dihydro-2H-1-benzopyran-3-yl)-5-(1,3-oxazol-5-yl)-1H-1,3-benzodiazole (54 mg).

Analytical HPLC Method A. [M+H$^+$] m/z: 336.0; Rt=2.66 min.

Compound (10): "Second" 2-(chroman-3-yl)-6-(oxazol-5-yl)benzo[d]oxazole

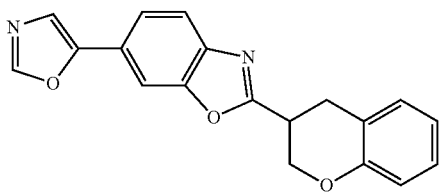 [SMILES: c1ccc2c(c1)CC(c1nc3ccc(-c4cnco4)cc3o1)CO2]

To a stirred solution of 6-bromo-2-(chroman-3-yl)-1H-benzo[d]imidazole (400 mg, 1.21 mmol) in a mix of 1,4-dioxane and water (4:1) (15 mL) were added 5-(4,4,5,5-tetramethyl-1,3,2-dioxaborolan-2-yl)oxazole (261 mg, 1.33 mmol) and Na$_2$CO$_3$ (258 mg, 2.43 mmol) at room temperature in a sealed tube. The resulting reaction mixture was degassed at room temperature for 20 min followed by the addition of PdCl$_2$(dppf)-dichloromethane complex (99 mg, 0.12 mmol) and stirred at 100° C. for 6 h. The reaction mixture was filtered and purified by Flash Chromatography to afford racemic 5-(2-(chroman-3-yl)-1H-benzo[d]imidazol-6-yl)oxazole 170 mg, 46%).

Chiral separation of 5-(2-(chroman-3-yl)-1H-benzo[d]imidazol-6-yl)oxazole using Chiral Separation Method B, yields "second" 2-(chroman-3-yl)-6-(oxazol-5-yl)benzo[d]oxazole (120 mg) characterized by retention time=11.3 min.

Analytical HPLC Method B. [M+H$^+$] m/z: 319.2; Rt=1.87 min.

Compound (11): "First" 2-(chroman-3-yl)-6-(oxazol-5-yl)benzo[d]oxazole

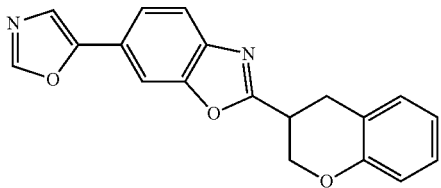 [SMILES: c1ccc2c(c1)CC(c1nc3ccc(-c4cnco4)cc3o1)CO2]

To a stirred solution of 6-bromo-2-(chroman-3-yl)-1H-benzo[d]imidazole (400 mg, 1.21 mmol) in a mix of 1,4-dioxane and water (4:1) (15 mL) were added 5-(4,4,5,5-tetramethyl-1,3,2-dioxaborolan-2-yl)oxazole (261 mg, 1.33 mmol) and Na$_2$CO$_3$ (258 mg, 2.43 mmol) at room temperature in a sealed tube. The resulting reaction mixture was degassed at room temperature for 20 min followed by the addition of PdCl$_2$(dppf)-dichloromethane complex (99 mg, 0.12 mmol) and stirred at 100° C. for 6 h. The reaction mixture was filtered and purified by Flash Chromatography to afford racemic 5-(2-(chroman-3-yl)-1H-benzo[d]imidazol-6-yl)oxazole 170 mg, 46%).

Chiral separation of 5-(2-(chroman-3-yl)-1H-benzo[d]imidazol-6-yl)oxazole using Chiral Separation Method B, yields "first" 2-(chroman-3-yl)-6-(oxazol-5-yl)benzo[d]oxazole (102 mg) characterized by retention time=10.1 min.

Analytical HPLC Method B. [M+H$^+$] m/z: 319.2; Rt=1.87 min.

The invention claimed is:
1. A compound of the formula (I)

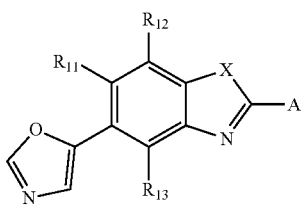

(I)

or a pharmaceutically acceptable salt, a racemic mixture, a corresponding enantiomer or, if applicable, a corresponding diastereomer thereof, wherein:
X is either NH or O,
$R_{11}$, $R_{12}$ and $R_{13}$ are independently selected from the group consisting of hydrogen, fluoro, chloro, trifluoromethyl, methyl and difluoromethoxy,
A is selected from the group consisting of formula (II), (III), (IV), (V), (VI), (VII) or (VIII)

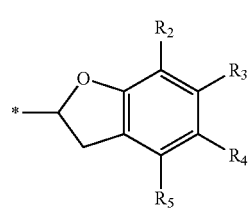

(II)

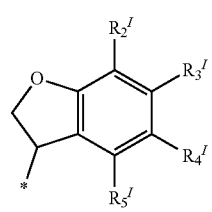

(III)

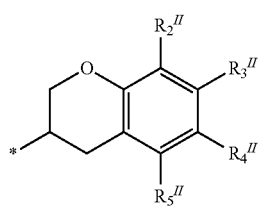

(IV)

-continued

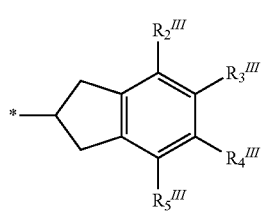
(V)

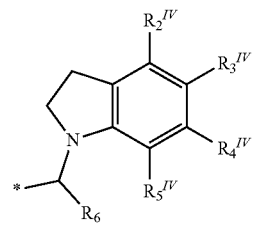
(VI)

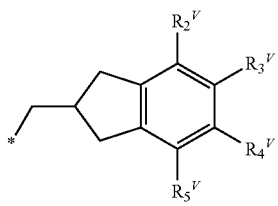
(VII)

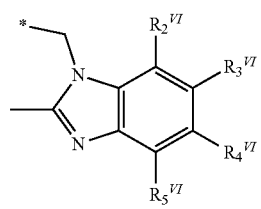
(VIII)

wherein,
"*" denotes the point of attachment to the remainder of the molecule, and
$R_2, R_3, R_4, R_5, R_2^I, R_3^I, R_4^I, R_5^I, R_2^{II}, R_3^{II}, R_4^{II}, R_5^{II}, R_2^{III}, R_3^{III}, R_4^{III}, R_5^{III}, R_2^{IV}, R_3^{IV}, R_4^{IV}, R_5^{IV}, R_2^V, R_3^V, R_4^V, R_5^V, R_2^{VI}, R_3^{VI}, R_4^{VI}$ and $R_5^{VI}$ are independently selected from the group consisting of hydrogen, a linear or branched alkyl having 1 to 3 carbon atoms, fluoro, chloro, bromo, methoxy, ethoxy, propoxy, trifluoromethyl, 2,2,2-trifluoroethyl and difluoromethoxy and
in formula (VI) $R_6$ is selected from the group consisting of hydrogen, a linear or branched alkyl having 1 to 3 carbon atoms, trifluoromethyl, and 2,2,2-trifluoroethyl.

2. The compound according to claim 1, wherein the compound of formula (I) the asymmetric center at ring position * of formula (II), (III), (IV) and (V) or on the side chain of formula (VI) has the configuration as depicted below, that is a compound of formula (Ii)

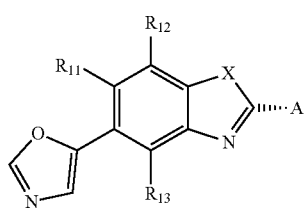
(Ii)

and X, $R_2, R_3, R_4, R_5, R_2^I, R_3^I, R_4^I, R_5^I, R_2^{II}, R_3^{II}, R_4^{II}, R_5^{II}, R_2^{III}, R_3^{III}, R_4^{III}, R_5^{III}, R_2^{IV}, R_3^{IV}, R_4^{IV}$, and $R_5^{IV}$ are as defined in claim 1.

3. The compound according to claim 1, wherein the asymmetric center ** in the compound of formula (I) has the configuration as depicted below

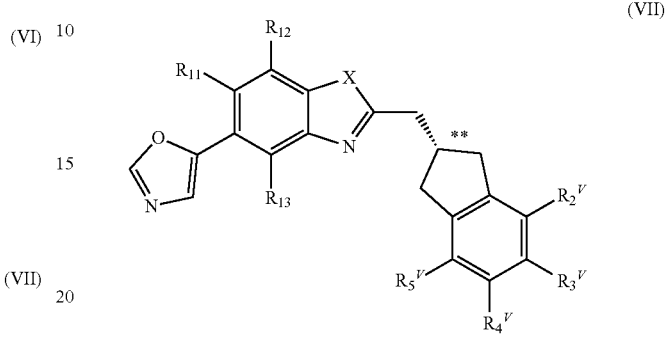
(VII)

wherein $R_2^V, R_3^V, R_4^V, R_5^V$, and $R_6$ are as defined in claim 1.

4. The compound according to claim 1, wherein the compound of formula (I) the asymmetric center at ring position * of formula (II), (III), (IV), (V) or on the side chain of formula (VI) has the configuration as depicted below, that is a compound of formula (Iii)

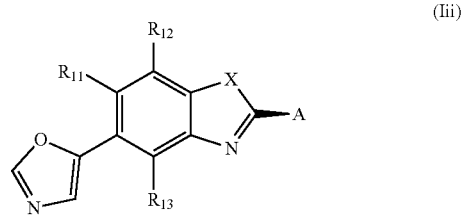
(Iii)

and X, $R_2, R_3, R_4, R_5, R_2^1, R_3^I, R_5^I, R_2^{II}, R_3^{II}, R_4^{II}, R_5^{II}, R_2^{III}, R_3^{III}, R_4^{III}, R_5^{III}, R_2^{IV}, R_3^{IV}, R_4^{IV}$, and $R_5^{IV}$ are as defined in claim 1.

5. The compound according to claim 1, wherein the asymmetric center ** in the compound of formula (I) has the configuration as depicted below

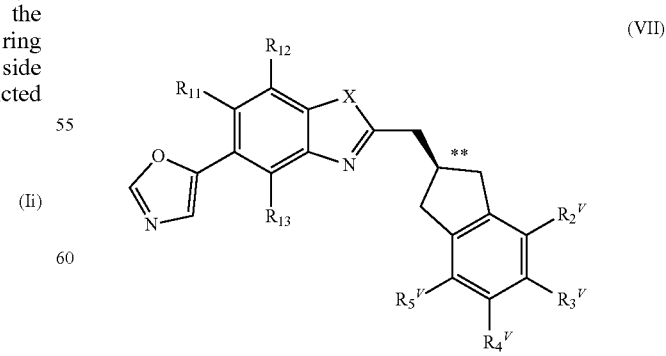
(VII)

wherein $R_2^V, R_3^V, R_4^V, R_5^V$, and $R_6$ are as defined in claim 1.

6. The compound according to claim 1, wherein the compound of formula (I) $R_{11}$, $R_{12}$ and $R_{13}$ are independently selected from the group consisting of hydrogen, chloro and fluoro.

7. The compound according to claim 1, wherein X is O.

8. The compound according to claim 1, wherein X is NH.

9. The compound according to claim 1, wherein A is unsubstituted.

10. The compound according to claim 1, wherein A is monosubstituted.

11. The compound according to claim 10, wherein A is monosubstituted, and one of $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{Iv}$, $R_2^{V}$, $R_3^{V}$, $R_4^{V}$, $R_5^{V}$, $R_2^{VI}$, $R_3^{VI}$, $R_4^{VI}$ and $R_5^{VI}$ is selected from the group consisting of chloro and fluoro and remaining ones are hydrogen.

12. The compound according to claim 1, wherein the compound of formula (I) is selected from the group consisting of compounds 1, 2, 3, 4, 5, 6, 7, 8, 9, 10 and 11:

| Comp. No. | Chemical structure |
|---|---|
| 1 | (structure) enantiomer with the shorter retention time from the chiral HPLC resolution |
| 2 | (structure) enantiomer with the longer retention time from the chiral HPLC resolution |
| 3 | (structure) (racemate) |
| 4 | (structure) (racemate) |
| 5 | (structure) (racemate) |
| 6 | (structure) (racemate) |
| 7 | (structure) |
| 8 | (structure) (racemate) |
| 9 | (structure) (racemate) |
| 10 | (structure) enantiomer with the longer retention time from the chiral HPLC resolution |
| 11 | (structure) enantiomer with the shorter retention time from the chiral HPLC resolution. |

13. A method of treating a disease involving the retinal pigment epithelium and/or reducing signs or symptoms of the disease, comprising administering the compound of the formula (I)

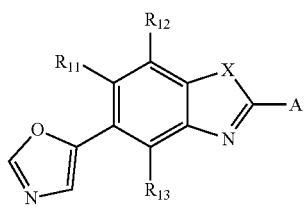

(I)

or a pharmaceutically acceptable salt, a racemic mixture, a corresponding enantiomer or, if applicable, a corresponding diastereomer thereof, wherein:

X is either NH or O, $R_{11}$, $R_{12}$ and $R_{13}$ are independently selected from the group consisting of hydrogen, fluoro, chloro, trifluoromethyl, methyl and difluoromethoxy, A is selected from the group consisting of formula (II), (III), (IV), (V), (VI), (VII) or (VIII)

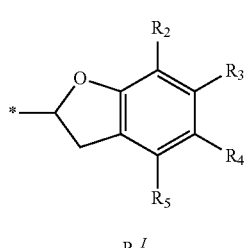

(II)

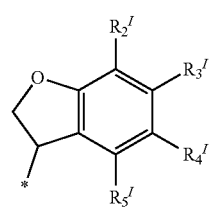

(III)

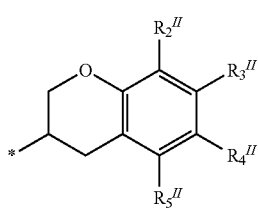

(IV)

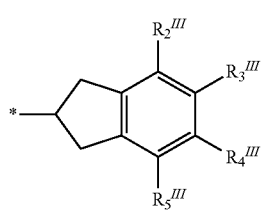

(V)

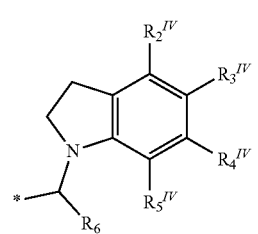

(VI)

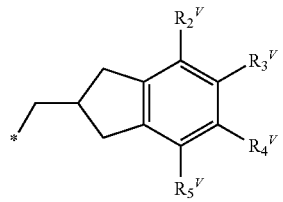

(VII)

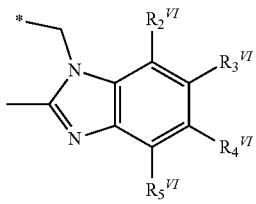

(VIII)

wherein,

"*" denotes the point of attachment to the remainder of the molecule, and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3^{VI}$, $R_4^{VI}$ and $R_5^{VI}$ are independently selected from the group consisting of hydrogen, a linear or branched alkyl having 1 to 3 carbon atoms, fluoro, chloro, bromo, methoxy, ethoxy, propoxy, trifluoromethyl, 2,2,2-trifluoroethyl and difluoromethoxy and in formula (VI) $R_6$ is selected from the group consisting of hydrogen, a linear or branched alkyl having 1 to 3 carbon atoms, trifluoromethyl, and 2,2,2-trifluoroethyl as active ingredient.

14. The method according to claim 13, wherein the compound of formula (I) is selected from the group consisting of compounds 1, 2, 3, 4, 5, 6, 7, 8, 9, 10 and 11:

| Comp. No. | Chemical structure |
|---|---|
| 1 | 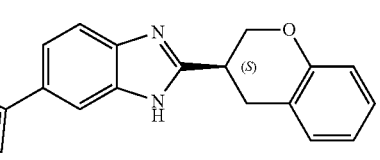 |
|  | enantiomer with the shorter retention time from the chiral HPLC resolution |
| 2 | 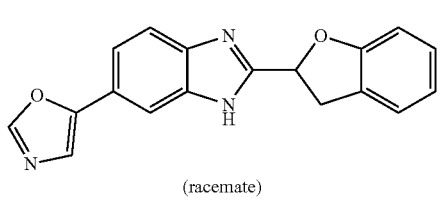 |
|  | enantiomer with the longer retention time from the chiral HPLC resolution |
| 3 | 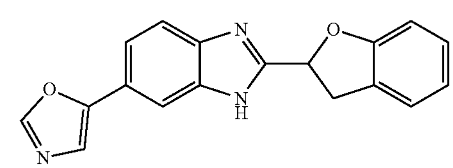 [SMILES: c1ccc2c(c1)CC(c1nc3ccc(-c4cnco4)cc3[nH]1)O2] |

-continued

| Comp. No. | Chemical structure |
|---|---|
| 4 | 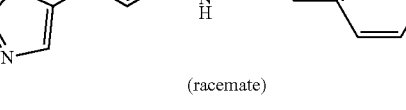<br>(racemate) |
| 5 | 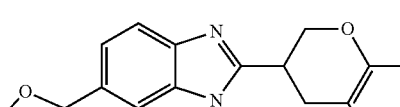<br>(racemate) |
| 6 | 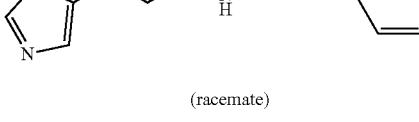<br>(racemate) |
| 7 | 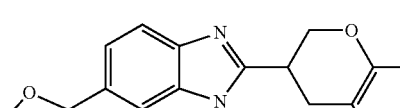 |
| 8 | 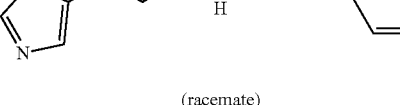<br>(racemate) |
| 9 | 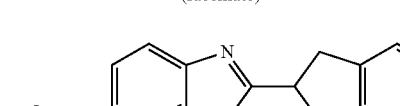<br>(racemate) |
| 10 | 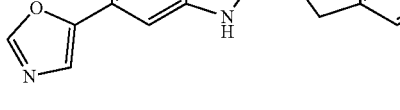<br>enantiomer with the longer retention time from the chiral HPLC resolution |

-continued

| Comp. No. | Chemical structure |
|---|---|
| 11 | 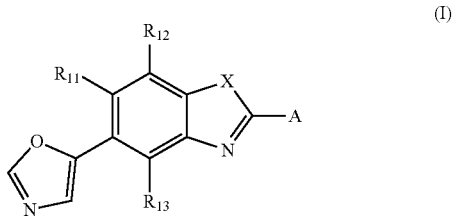<br>enantiomer with the shorter retention time from the chiral HPLC resolution. |

15. The method according to claim 13, wherein the retinal cells are regenerated via the proliferation and/or differentiation of retinal pigment epithelium cells.

16. The method according to claim 13, wherein the retinal disease is selected from the group consisting of a disease leading to atrophy, degeneration or death of the retinal pigment epithelium.

17. The method according to claim 16, wherein the retinal disease is selected from the group consisting of early age-related macular degeneration, dry age-related macular degeneration, geographic atrophy (GA) and wet age-related macular degeneration.

18. The method according to claim 17, wherein the retinal disease is dry age-related macular degeneration.

19. The method according to claim 13, wherein the retinal disease is selected from the group consisting of Best disease, autosomal recessive bestrophinopathy (ARB), gyrate atrophy, North Carolina macular dystrophy, central areolar choroidal dystrophy (CACD), Sorsby macular dystrophy, familial dominant drusen, cuticular or basal laminar drusen, retinopathy of prematurity, myopic degeneration, polypoidal choroidal vasculopathy (PCV), central serious retinopathy, angioid streaks, retinal detachment, retinal dialysis, Vogt-Koyanagi-Harada (VKH), acute posterior multifocal placoid pigment epitheliopathy (APMPPE), persistent placoid maculopathy (PPM) relentless placoid chorioretinopathy (RPC), serpiginous choroiditis, serpiginous-like choroiditis, multiple evanescence white dot syndrome (MEWDS) or Birdshot uveitis, toxoplasmosis, toxocariasis, rubella, Behçets disease, choroidal hemangioma, trauma, choroidal rupture, idiopathic retinitis—vasculitis—aneurysms and neuroretinitis (IRVAN), sympathetic ophthalmia, post-operative inflammation, or non-arteritic ischemic optic neuropathy and retinal degeneration associated with systemic disease.

20. A pharmaceutical composition comprising a compound of the formula (I)

or a pharmaceutically acceptable salt, a racemic mixture, a corresponding enantiomer or, if applicable, a corresponding diastereomer thereof, wherein:

X is either NH or O, $R_{11}$, $R_{12}$ and $R_{13}$ are independently selected from the group consisting of hydrogen, fluoro, chloro, trifluoromethyl, methyl and difluoromethoxy, A is selected from the group consisting of formula (II), (III), (IV), (V), (VI), (VII) or (VIII)

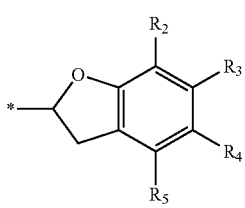
(II)

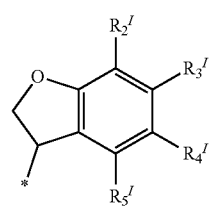
(III)

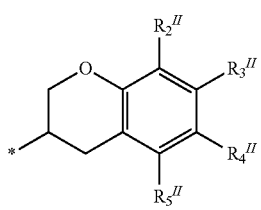
(IV)

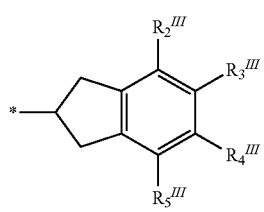
(V)

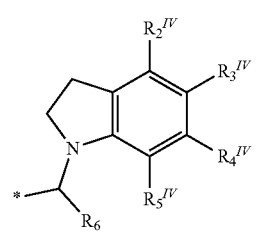
(VI)

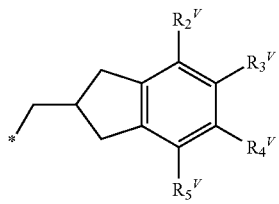
(VII)

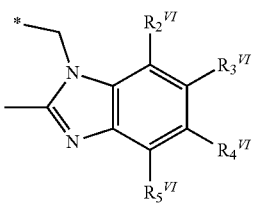
(VIII)

wherein,

"*" denotes the point of attachment to the remainder of the molecule, and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$, $R_2^{VI}$, $R_3^{VI}$, $R_4^{VI}$ and $R_5^{VI}$ are independently selected from the group consisting of hydrogen, a linear or branched alkyl having 1 to 3 carbon atoms, fluoro, chloro, bromo, methoxy, ethoxy, propoxy, trifluoromethyl, 2,2,2-trifluoroethyl and difluoromethoxy and in formula (VI) $R_6$ is selected from the group consisting of hydrogen, a linear or branched alkyl having 1 to 3 carbon atoms, trifluoromethyl, and 2,2,2-trifluoroethyl as a therapeutically active substance and a pharmaceutically acceptable carrier and/or adjuvant.

21. The pharmaceutical composition according to claim 20, wherein the pharmaceutical preparation is suitable for intraocular injection or for topical ophthalmic applications.

22. The pharmaceutical composition according to claim 20, further comprising one or more additional therapeutic agents.

23. The pharmaceutical composition according to claim 20, wherein the pharmaceutical composition provides controlled release properties.

24. The method according to claim 19, wherein the systemic disease is diabetes mellitus, sickle cell disease or radiation retinopathy.

* * * * *